(12) United States Patent
Callister et al.

(10) Patent No.: US 8,414,901 B2
(45) Date of Patent: *Apr. 9, 2013

(54) CANINE LYME DISEASE VACCINE

(75) Inventors: Steven M. Callister, Onalaska, WI (US);
Rhonda LaFleur, Elkhorn, NE (US);
Terri L. Wasmoen, Elkhorn, NE (US)

(73) Assignee: Intervet Inc., Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/358,905

(22) Filed: Jan. 26, 2012

(65) Prior Publication Data

US 2012/0141530 A1 Jun. 7, 2012

Related U.S. Application Data

(63) Continuation of application No. 11/933,583, filed on Nov. 1, 2007, now Pat. No. 8,137, 678.

(60) Provisional application No. 60/864,258, filed on Nov. 3, 2006.

(51) Int. Cl.
*A61K 39/02* (2006.01)
*C07K 16/12* (2006.01)

(52) U.S. Cl. ............... 424/234.1; 424/184.1; 530/387.1

(58) Field of Classification Search .................. None
See application file for complete search history.

(56) References Cited

U.S. PATENT DOCUMENTS

| | | | |
|---|---|---|---|
| 4,002,736 A | 1/1977 | Pankratz |
| 4,721,617 A | 1/1988 | Johnson |
| 5,178,859 A | 1/1993 | Simon et al. |
| 5,246,844 A | 9/1993 | Norris et al. |
| 5,385,826 A | 1/1995 | Schell et al. |
| 5,434,077 A | 7/1995 | Simon |
| 5,436,000 A | 7/1995 | Barbour |
| 5,523,089 A | 6/1996 | Bergstrom et al. |
| 5,530,103 A | 6/1996 | Livey et al. |
| 5,582,829 A | 12/1996 | Alliger et al. |
| 5,582,990 A | 12/1996 | Bergstrom et al. |
| 5,585,102 A | 12/1996 | Barbour et al. |
| 5,656,451 A | 8/1997 | Flavell et al. |
| 5,683,702 A | 11/1997 | Becker et al. |
| 5,686,078 A | 11/1997 | Becker et al. |
| 5,686,267 A | 11/1997 | Simon et al. |
| 5,688,512 A | 11/1997 | Bergstrom et al. |
| 5,777,095 A | 7/1998 | Barbour et al. |
| 5,780,030 A | 7/1998 | Simon et al. |
| 5,856,447 A | 1/1999 | Simon et al. |
| 6,045,804 A | 4/2000 | Persing |
| 6,054,296 A | 4/2000 | Bergstrom et al. |
| 6,068,842 A | 5/2000 | Bergstrom et al. |
| 6,077,515 A | 6/2000 | Barbour et al. |
| 6,083,722 A | 7/2000 | Bergstrom et al. |
| 6,086,901 A | 7/2000 | O'Hagan et al. |
| 6,090,586 A | 7/2000 | Bergstrom et al. |
| 6,143,788 A | 11/2000 | Getman et al. |
| 6,143,872 A | 11/2000 | Barbour et al. |
| 6,150,556 A | 11/2000 | Getman et al. |
| 6,153,194 A | 11/2000 | Skare et al. |
| 6,183,986 B1 | 2/2001 | Bergstrom et al. |
| 6,203,798 B1 | 3/2001 | Bergstrom et al. |
| 6,204,018 B1 | 3/2001 | Bergstom et al. |
| 6,210,676 B1 | 4/2001 | Callilster et al. |
| 6,221,363 B1 | 4/2001 | Livey et al. |
| 6,296,849 B1 | 10/2001 | Sadziene et al. |
| 6,300,101 B1 | 10/2001 | Sadziene et al. |
| 6,303,129 B1 | 10/2001 | Alliger et al. |
| 6,306,405 B1 | 10/2001 | O'Hagan et al. |
| 6,312,915 B1 | 11/2001 | Nelson et al. |
| 6,316,005 B1 | 11/2001 | Korshus et al. |
| 6,316,496 B1 | 11/2001 | Getman et al. |
| 6,368,603 B1 | 4/2002 | Jarecki-Black |
| 6,388,132 B1 | 5/2002 | Getman et al. |
| 6,458,370 B1 | 10/2002 | O'Hagan et al. |
| 6,464,985 B1 | 10/2002 | Callister et al. |
| 6,486,130 B1 | 11/2002 | Livey et al. |
| 6,509,017 B1 | 1/2003 | Bergstrom et al. |
| 6,517,838 B1 | 2/2003 | Hook et al. |
| 6,592,875 B1 | 7/2003 | McMichael |
| 6,613,331 B1 | 9/2003 | Simon et al. |
| 6,660,274 B2 | 12/2003 | Philipp |
| 6,683,210 B2 | 1/2004 | Getman et al. |
| 6,761,891 B1 | 7/2004 | Simon et al. |
| 6,814,970 B2 | 11/2004 | Sadziene et al. |
| 6,855,492 B2 | 2/2005 | O'Hagan et al. |
| 6,861,539 B1 | 3/2005 | Getman et al. |

(Continued)

FOREIGN PATENT DOCUMENTS

| | | |
|---|---|---|
| DE | 10 2006 045 252 | 4/2008 |
| EP | 0 418 827 | 9/1990 |
| EP | 0 465 204 | 1/1992 |
| EP | 0 565 208 | 10/1992 |
| EP | 0 522 560 | 1/1993 |
| EP | 0 540 457 | 5/1993 |
| EP | 0 633 028 | 1/1995 |
| EP | 0 633 313 | 1/1995 |
| EP | 0 643 974 | 5/1995 |
| EP | 0 650 527 | 5/1995 |
| EP | 0 711 563 | 5/1996 |
| EP | 0 445 135 | 3/1997 |
| EP | 0 813 543 | 12/1997 |
| EP | 0 988 051 | 3/2000 |
| EP | 1 016 416 | 7/2000 |
| EP | 1 042 001 | 10/2000 |
| EP | 1 080 109 | 3/2001 |
| WO | 90/04411 | 5/1990 |
| WO | 92/00055 | 1/1991 |
| WO | 92/12235 | 7/1992 |

(Continued)

OTHER PUBLICATIONS

Obonyo, et al., *Borrelia burgdorferi* in Tick Cell Culture Modulates Expression of Outer Surface Proteins A and C in Response to Temperature, vol. 37, No. 7, pp. 2137-2141 (1999).

(Continued)

*Primary Examiner* — Padma V Baskar
(74) *Attorney, Agent, or Firm* — Michael D. Davis

(57) ABSTRACT

The present invention provides a vaccine for canine Lyme disease and methods of making and using the vaccine alone, or in combinations with other protective agents.

23 Claims, 7 Drawing Sheets

U.S. PATENT DOCUMENTS

| | | | |
|---|---|---|---|
| 6,872,550 | B1 | 3/2005 | Livey et al. |
| 7,094,391 | B1 | 8/2006 | Barbour et al. |
| 7,161,033 | B2 | 1/2007 | Getman et al. |
| 7,339,078 | B2 | 3/2008 | Getman et al. |
| 7,393,630 | B2 | 7/2008 | O'Hagan et al. |
| 8,137,678 | B2 * | 3/2012 | Callister et al. ............ 424/234.1 |
| 2001/0036658 | A1 | 11/2001 | Phillips et al. |
| 2004/0197339 | A1 | 10/2004 | Brown |
| 2006/0188524 | A1 | 8/2006 | Hu et al. |
| 2007/0141130 | A1 | 6/2007 | Villanueva et al. |

FOREIGN PATENT DOCUMENTS

| | | |
|---|---|---|
| WO | 93/04175 | 3/1993 |
| WO | 93/08306 | 4/1993 |
| WO | 93/24145 | 12/1993 |
| WO | 94/06463 | 3/1994 |
| WO | 94/19697 | 9/1994 |
| WO | 94/25596 | 11/1994 |
| WO | 95/27504 | 10/1995 |
| WO | 95/35119 | 12/1995 |
| WO | 97/15600 | 5/1997 |
| WO | 97/26273 | 7/1997 |
| WO | 98/39028 | 9/1998 |
| WO | 98/56414 | 12/1998 |
| WO | 99/00413 | 1/1999 |
| WO | 99/14345 | 3/1999 |
| WO | 99/30737 | 6/1999 |
| WO | 99/32502 | 7/1999 |
| WO | 99/32602 | 7/1999 |
| WO | 99/61048 | 12/1999 |
| WO | 99/61473 | 12/1999 |
| WO | 00/06745 | 2/2000 |
| WO | 00/22134 | 4/2000 |
| WO | 00/77041 | 12/2000 |
| WO | 00/78345 | 12/2000 |
| WO | 01/78650 | 10/2001 |
| WO | 03/024354 | 3/2003 |
| WO | 2006/038115 | 4/2006 |
| WO | 2008/043774 | 4/2008 |
| WO | 2008/063240 | 5/2008 |

OTHER PUBLICATIONS

Ohnishi, et al., "Antigenic and genetic heterogenity of *Borrelia burgdorferi* populations transmitted by ticks", PNAS, vol. 98, No. 2, pp. 670-675 (2001).

Ornstein, et al., "Characterization of Lyme *Borreliosis* Isolates from Patients with Erythema Migrans and Neuroborreliosis in Southern Sweden", Journal of Clinical Microbiology, vol. 39, No. 4, pp. 1294-1298 (2001).

Pal, et al., "Attachment of *Borrelia burgdorferi* within Ixodes scapularis mediated by outer surface protein A", The Journal of Clinical Investigation, vol. 106, No. 4, pp. 561-569 (2000).

Rousselle, et al., "Borreliacidal Antibody Production against Outer Surface Protein C of *Borrelia burgdorferi*", The Journal of Infectious Diseases, vol. 178, No. 3, pp. 733-741 (1998).

Schutzer, et al., "Detection of Lyme Disease after OspA Vaccine", The New England Journal of Medicine, vol. 337, No. 11, pp. 794-795 (1997).

Schwan, et al., "Induction of an outer surface protein on *Borrelia burgdorferi* during tick feeding", Proc. Natl. Acad. Sci., vol. 92, pp. 2909-2913 (1995).

Schwan, et al., "Temporal regulation of outer surface proteins of the Lyme-disease spirochaete *Borrelia burgdorferi*", Biochemical Transactions, vol. 31, Part 1, pp. 108-112 (2003).

Sen, et al., Microbes and Infection, vol. 5, pp. 869-878, 2003.

Simpson, et al., "Reactivity of Human Lyme Borreliosis Sera with a 39-Kilodalton Antigen Specific to *Borrelia burgdorferi*", Journal of Clinical Microbiology, vol. 28, No. 6, pp. 1329-1337 (1990).

Srivastava, et al., "Reciprocal Expression of OspA and ospC in Single Cells of *Borrelia burgdorferi*", Journal of Bacteriology, vol. 190, No. 10, pp. 3429-3433 (2008).

Stewart, et al., "Delineating the Requirement for the *Borrelia burgdorferi* Virulence Factor OspC in the Mammalian Host", Infectio and Immunity, vol. 74, No. 6, pp. 3547-3553 (2006).

Straubinger, et al., "Protection against tick-transmitted Lyme disease in dogs vaccinated with a multiantingenic vaccine", Vaccine, vol. 20, No. 1-2, pp. 181-193 (2002).

Summers, et al., "Histopathological Studies of Experimental Lyme Disease in the Dog", J. Comp. Path., vol. 133, pp. 1-13 (2005).

Telford, et al., "Protection against Antigenically Variable *Borrelia burgdorferi* Conferrred by Recombinant Vaccines", J. Exp. Med., vol. 178, pp. 755-758 (1993).

Tilly, et al., "*Borrelia burgdorferi* OspC Protein Required Exclusively in a Crucial Early Stage of Mammalian Infection", Infection and Immunity, vol. 74, No. 6, pp. 3554-3564 (2006).

Tokarz, et al., Combined Effects of Blood and Temperature Shift on *Borrelia burgdorferi* Gene Expression as Determined by Whole Genome DNA Array, vol. 72, No. 9, pp. 5419-5432 (2004).

Topfer, et al., "Characterization of the humoral immune response in dogs after vaccination against the Lyme borreliosis agent A study with five commercial vaccines using two different vaccination schedules", Vaccine, vol. 25, No. 2, pp. 314-326 (2007).

Wikle, et al., "Canine Lyme Disease: One-Year Duration of Immunity Elicited With a Canine OspA Monovalent Lyme Vaccine", Intern J. Appl. Res. Vet. Med., vol. 4, No. 1, pp. 23-28 (2006).

Wilske, et al., "Immunological and Molecular Variability of OspA and OsPC. Implications for *Borrelia* Vaccine Development", Infection, vol. 24, No. 2, pp. 208-212 (1996).

Wilske, et al., Immunological and Molecular Polymorphisms of OspC, an Immunodominant Major Outer Surface Protein of B *Borrelia burgdorferi*, Infection and Immunity, vol. 61, No. 5, pp. 2182-2191 (1993).

Wilske, et al., Med Microbiol Immunol, vol. 184, pp. 195-201 (1996).

PCT International Search Report dated Aug. 11, 2008 for corresponding PCT Application No. PCT/US2007/023101.

Anderson, et al., "Novel *Borrelia burgdorferi* Isolates from Ixodes scapularis and Ixodes dentatus Ticks Feeding on Humans" Journal of Clinical Microbiology, vol. 34, No. 3, pp. 524-529 (1996).

Barbour, et al., "Biology of *Borrelia* Species", Microbiological Reviews, vol. 50, No. 4, pp. 381-400 (1986).

Barbour, et al., "Heterogeneity of Major Proteins in Lyme Disease Borreliae: A Molecular Analysis of North American and European Isolates", The Journal of Infectious Diseases, vol. 152, No. 3, pp. 478-484 (1985).

Baranton, et al., "Delineation of *Borrelia burgdorferi* Sensu Strictor, *Borrelia garinii* sp. nov., and Group VS461 Associated with Lyme Borreliosis", International Journal of Systematic Bacteriology, vol. 42, No. 3, pp. 378-383 (1992).

Bockenstedt, et al., *Borrelia burgdorferi* Strain-Specific Osp C-Mediated Immunity in Mice, Infection and Immunity, vol. 65, No. 11, pp. 4661-4667 (1997).

Brown, et al., "Multicomponent Lyme vaccine: Three is not a crowd", Vaccine, vol. 23, No. 28, pp. 3687-3696 (2005).

Buckles, et al., "Analysis of Antibody Response in Humans to the Type A OspC Loop 5 Domain and Assessment of the Potential Utility of the Loop 5 Epitope in Lyme Disease Vaccine Development", Clinical and Vaccine Immunology, vol. 13, No. 10, pp. 1162-1165 (2006).

Callister, et al., "Effects of Bovine Serum Albumin on the Ability of Barbour-Stoenner-Kelly Medium to Detect *Borrelia burgdorferi*", Journal of Clinical Microbiology, vol. 28, No. 2, pp. 363-365 (1990).

Callister, et al., "Characterization of the Borreliacidal Antibody Response to *Borrelia burgdorferi* in Human: A Serodiagnostic Test", The Journal of Infectious Diseases, vol. 167, pp. 158-164 (1993).

Callister, et al., "Detection of Borreliacidal Antibodies by Flow Cytometry", Arch. Intern. Med., vol. 154, pp. 1625-1632 (1994).

Callister, et al., "Sensitivity and Specificity of the Borreliacidal-Antibody Test during Early Lyme Disease: a "Gold Standard"?", Clinical and Diagnostic Laboratory Immunology, vol. 3, No. 4, pp. 399-402 (1996).

Callister, et al., Ability of the Borreliacidal Antibody Test to Confirm Lyme Disease in Clinical Practice, Clinical and Diagnostic Laboratory Immunology, vol. 9, No. 4, pp. 908-912 (2002).

Callister et al., Journal of Clinical Microbiology, vol. 38, pp. 3670-3674 (2000).

Carrie et al., Infection and Immunity, vol. 61, pp. 5115-5122 (1993).

Chu, et al., "Immunogenicity and efficacy study of a commercial *Borrelia burgdorferi* bacterin", JAVMA, vol. 201, No. 3, pp. 403-411 (1992).

Duval, et al., "Vaccine-Associated Immune-Mediated Hemolytic Anemia in the Dog", Journal of Veterinary Internal Medicine, vol. 10, No. 5, pp. 290-295 (1996).

Earnhart, et al., "OspC Phylogenetic Analyses Support the Feasibility of a Broadly Protective Polyvalent Chimeric Lyme Disease Vaccine", Clinical and Vaccine Immunology, vol. 14, No. 5, pp. 628-634 (2007).

Earnhart et al, "An Octavalent Lyme Disease Vaccine Induces Antibodies That Recognize All Incorporated OspC Type-Specific Sequences", Human Vaccines, vol. 3, No. 6, pp. 281-289 (2007).

Earnhart et al, "Development of an Osp-C Based Tetravalent, Recombinant, Chimeric Vaccinogen that Elicits Bactericidal Antibody Against Diverse Lyme Disease Spirochete Strains", Vaccine, vol. 25, pp. 466-480 (2007).

Earnhart et al., Infection and Immunity, vol. 73, pp. 7869-7877 (2005).

Feng et al, "P55, an Immunogenic but Nonprotective 55-Kilodalton *Borrelia burgdorferi* Protein in Murine Lyme Disease", Infection and Immunity, vol. 64, No. 1, pp. 363-365 (1996).

Fikrig, et al., "Elimination of *Borrelia burgdorferi* from vector ticks feeding on OspA-immunized mice", Proc. Natl. Acad. Sci., vol. 89, pp. 5418-5421 (1992).

Fikrig, et al., "Selection of Variant *Borrelia burgdorferi* Isolates from Mice Immunized with Outer Surface Protein A or B", Infection and Immunity, vol. 63, No. 5, pp. 1658-1662 (1995).

Gilmore, et al., "The Protective Capability of the *Borrelia burgdorferi* Outer Surface Protein C is Dependent on the Conformational Structure of the Immunogen" Abstracts of the General Meeting of the American Society for Microbiology, vol. 98, p. 222 (1998).

Gilmore, et al., "Outer Surface Protein C (OspC) but Not P39, Is a Protective Immunogen against a Tick-Transmitted *Borrelia burgdorferi* Challenge: Evidence for a Conformational Protective Epitope in OspC", Infection and Immunity, vol. 64, No. 6, pp. 2234-2239 (1996).

Grimm, et al., "Outer-surface protein C of the Lyme disease spirochete: A protein induced in ticks for infection of mammals", PNAS, vol. 101, No. 9 pp. 3142-3147 (2004).

Hagman et al, "Decorin-Binding Protein A (DbpA) of *Borrelia burgdorferi* Is Not Protective When Immunized Mice Are Challenged via Tick Infestation and Correlates with the Lack of DbpA Expression by *B. burgdorferi* in Ticks", Infection and Immunity, vol. 68, No. 8, pp. 4759-4764 (2000).

Hanincova, et al., "Epidemic Spread of Lyme Borreliosis, Northeastern United States", Emerging Infectious Diseases, vol. 12, No. 4, pp. 604-611 (2006).

Hauser et al., Clinical and Diagnostic Laboratory Immunology, pp. 456-462, 2012.

Hovius, et al., "Antibodies against Specific Proteins of and Immobilizing Activity against Three Strains of *Borrelia burgdorferi* Sensu Lato Can Be Found in Symptomatic but Not in Infected Asymptomatic Dogs", Journal of Clinical Microbiology, vol. 38, No. 7, pp. 2611-2621 (2000).

Hu, et al., "Comparison in the immunological properties of *Borrelia burgdorferi* isolates from Ixodes ricinus derived from three endemic areas in Switzerland", Epidermiol. Infect. vol. 112, No. 3, pp. 533-542 (1994).

Ikushima, et al., "Specific immune response to a synthetic peptide derived from outer surface protein C of *Borrelia burgdorferi* predicts protective borreliacidal antibodies", FEMS Immunology and Medical Microbiology, vol. 29, pp. 15-21 (2000).

Jacobson, et al., "Lyme Disease: Laboratory Diagnosis of Infected and Vaccinated Symptomatic Dogs", Seminars in Veterinary Medicine and Surgery (Small Animal), vol. 11, No. 3, pp. 172-182 (1996).

Jobe, et al., "Ability of Canine Lyme Disease Vaccine to Protect Hamsters against Infection with Several Isolates of *Borrelia burgdorferi*", vol. 32, No. 3, pp. 618-622 (1994).

Jobe, et al., "C-Terminal Region of Outer Surface Protein C Binds Borreliacidal Antibodies in Sera from Patients with Lyme Disease", vol. 10, No. 4, pp. 573-578 (2003).

Johnson, et al., "Passive Immunization of Hamsters against Experimental Infection with the Lyme Disease Spirochete", Infection and Immunity, vol. 53, No. 3, pp. 713-714 (1986).

Johnson, et al., "Active Immunization of Hamsters against Experimental Infection with *Borelia burgdorferi*", Infection and Immunity, vol. 54, No. 3, pp. 897-898 (1986).

Krause, et al., "Vaccination against Lyme borreliosis", Infection, vol. 29, Supplemental 1, p. 37 (2001).

Kurtti, et al., "Resistance to Tick-Borne Spirochete Challenge Induced by *Borrelia burgdorferi* Strains That Differ in Expression of Outer Surface Proteins", Infection and Immunity, vol. 64, No. 10, pp. 4148-4153 (1996).

Labreche, et al., "Ability of Borreliacidal Anti-*Borrelia burgdorferi* 50772 Antibodies to Provide Protection against Hamster-Adapted Lyme Disease Spirochetes", Abstracts American Society for Microbiology, Session No. 213, E. Abstract E-49, p. 196 (2002).

Lafleur, et al., "Bacterin That Induces Anti-OspA and Anti-OspC Borreliacidal Antibodies Provides a High Level of Protection against Canine Lyme Disease", Clinical and Vaccine Immunology, vol. 16, No. 2, pp. 253-259 (2009).

LaFleur, et al, "One-Year Duration of Immunity Induced by Vaccination with a Canine Lyme Disease Bacterin", Clinical and Vaccine Immunology, vol. 17, No. 5, pp. 870-874 (2010).

Levy, et al., "Performance of a *Borrelia burgdorferi* bacterin in borreliosis-endemic areas", JAVMA, vol. 202, No. 11, pp. 1834-1838 (1993).

Lovrich, et al., "Seroprotective Groups among Isolates of *Borrelia burgdorferi*", Infection and Immunity, vol. 61, No. 10, pp. 4367-4374 (1993).

Lovrich, et al., "Borreliacidal OspC Antibodies Specific for a Highly Conserved Epitope Are Immunodominant in Human Lyme Disease and Do Not Occur in Mice or Hamsters", Clinical and Diagnostic Laboratory Immunology, vol. 12, No. 6, pp. 746-751 (2005).

Lovrich, et al., "Abilities of OspA Proteins from Different Seroprotective Groups of *Borrelia burgdorferi* to Protect Hamsters from Infection", Infection and Immunity, vol. 63, No. 6, pp. 2113-2119 (1995).

Lovrich, et al, "Borreliacidal OspC Antibody Response of Canines with Lyme Disease Differs Significantly from That of Humans with Lyme Disease", Clinical and Vaccine Immunology, vol. 14, No. 5, pp. 635-637 (2007).

Luft, et al, "A New Multi-Target OspA-OspC Vaccine for Lyme Disease", Interscience Conference on Antimicrobial Agents and Chemotherapy (Sep. 17-20, 2000) [Abstract].

Ma, et al., "Intracellular Localization of *Borrelia burgdorferi* within Human Endothelial Cells", Infection and Immunity, vol. 59, No. 2, pp. 671-678 (1992).

Ma, et al., Safety, efficacy, and immunogenicity of a recombinant Osp subunit canine Lyme disease vaccine, Vaccine, vol. 14, No. 14, pp. 1366-1374 (1996).

* cited by examiner

CANINE LYME DISEASE VACCINE

CROSS-REFERENCE TO RELATED APPLICATIONS

This application is a continuation of co-pending non-provisional application U.S. Ser. No. 11/933,583, filed on Nov. 1, 2007 that claims priority under 35 U.S.C. §119(e) of provisional application U.S. Ser. No. 60/864,258 filed Nov. 3, 2006, the contents of both of which are hereby incorporated by reference in their entireties.

FIELD OF THE INVENTION

The present invention relates to a vaccine for canine Lyme disease. Methods of making and using the vaccine alone or in combinations with other protective agents are also provided.

BACKGROUND

Canine Lyme disease is caused by infection with *Borrelia* species (spp.) spirochetes, including primarily *B. burgdorferi* sensu strict (ss) in the United States and *B. burgdorferi* ss, *B. garinii*, and *B. afzelii* in Europe (Baranton et al., *Int. J. Sys. Bacteriol.* 1992, 42:378-383; Hovius et al., *J. Clin. Microbiol.* 2000, 38:2611-2621). The spirochetes are transmitted as the infected *Ixodes* spp. ticks obtain a blood meal, and the resulting infection in canines results in clinical signs ranging from subclinical synovitis to acute arthritis and arthralgia (Jacobson et al., *Semin. Vet. Med. Surg.* 1996, 11:172-182; Summers et al, *J. Comp. Path.* 2005, 133:1-13). Importantly, the incidence of canine Lyme disease cases continues to increase annually coincident with increased numbers of human cases (Haninkova et al., *Emerg. Infect. Dis.* 2006, 12:604-610).

The antibodies produced in response to infection with *Borrelia* spp. have two distinct functions, but heretofore, both responses could be ineffective at eliminating sequestered spirochetes from a mammalian host. A number of explanations have been postulated for this defect in the normal immune response to natural infection, including antigenic variation (Schwan, *Biochem. Soc. Trans.* 2003, 31:108-112; Tokarz et al., *Infect. Immun.* 2004, 72:5419-5432), host mimicry (Barbour et al. *Microbiol. Rev.* 1986, 50:381-400), and intracellular localization (Ma et al., *Infect. Immun.* 1991, 59:671-678).

The most common humoral immune response is the production of non-specific binding/opsonizing (coating) antibodies that "mark" the spirochete for ingestion by phagocytic cells. Unfortunately, opsonizing antibodies are induced by several proteins common to other microorganisms (viz. 41 kDa proteins that comprise bacterial flagella), making their value for vaccination-induced antibody-mediated immunity, at best, questionable.

A second common immune response is the production of borreliacidal (lethal) antibodies. In contrast to opsonizing antibodies, borreliacidal antibodies recognize epitopes on only a few *Borrelia* spp. proteins. After binding to the specific target on the spirochete, the borreliacidal antibodies most commonly induce complement to form a membrane attack complex that kills the organism without the necessity of scavenging by phagocytic cells.

The canine Lyme disease bacterins presently employed in vaccines were developed to provide protection by inducing OspA borreliacidal antibodies (Hsien-Chu et al., *JAVMA* 1992, 201:403-411; Ma et al., *Vaccine* 1996, 14:1366-1374; Wikle et al., *Intern. J. Appl. Res. Vet. Med.* 2006, 4:23-28; Straubinger et al., *Vaccine* 2001, 20:181-193) that kill the OspA-expressing spirochetes in the infected ticks as the parasites procure a bloodmeal (Fikrig et al., *Proc. Natl. Acad. Sci. USA* 1992, 89:5418-5421). Straubinger et al., (*Vaccine* 2002, 20:181-193) has reported that a whole cell vaccine induced significantly higher titers of borreliacidal antibodies than a recombinant OspA. Although such vaccines have been reasonably successful, vaccination failures have been reported (Levy et al. *JAVMA* 1993, 202:1834-1838; Ma et al., *Vaccine* 1996, 14:1366-1374; Schutzer et al., *N. Engl. J. Med.* 1997, 337:794-795).

It is now understood that the OspA borreliacidal antibodies generated often fail to sterilize feeding ticks, because the antibodies only recognize *B. burgdorferi* ss (Jobe et al., *J. Clin. Microbiol.* 1994, 32:618-622; Lovrich et al., *Infect. Immun.* 1995, 63:2113-2119) that are expressing OspA, and the ticks are commonly infected with *B. burgdorferi* ss spirochetes that are not expressing OspA (Fikrig et al., *Infect. Immun.* 1995, 63:1658-1662; Ohnishi et al., *Proc. Natl. Acad. Sci.* 2001, 98:670-675). In addition, the ticks are commonly also infected with other pathogenic *Borrelia* spp. including *B. afzelii* and *B. garinii* (Ornstein et al., *J. Clin. Microbiol.* 2001, 39:1294-1298), while the OspA antibodies are genospecies specific (Lovrich et al., *Infect. Immun.* 1995, 63:2113-2119). Moreover, the 'window of opportunity' for protection by OspA borreliacidal antibodies is limited even when the spirochetes are susceptible, because the expression of OspA, which mediates attachment to the tick midgut (Pal et al., *J. Clin. Invest.* 2000, 106:561-569), is down-regulated shortly after the infected tick begins feeding (Schwan et al., *Proc. Natl. Acad. Sci. USA* 1995, 92:2909-2913).

*B. burgdorferi* ss OspC is another potential target for borreliacidal antibody-mediated immunity (Rousselle et al., *J. Infect. Dis.* 1998, 178:733-741). This protein appears to have an epitope that is responsible for inducing borreliacidal antibodies and is conserved among the pathogenic *Borrelia* spp. (Lovrich et al., *Clin. Diagn. Lab. Immunol.* 2005, 12:746-751). Although the specific function of the OspC protein remains unknown, it has been suggested that OspC expression is required for infection of mammals, but not for infection of ticks (Grimm et al., 2004, *Proc. Natl. Acad. Sci.* 101(9):3142-3147). In any event, Lyme disease spirochetes express OspC shortly after the tick begins feeding (Schwan et al., *Proc. Natl. Acad. Sci. USA* 1995, 92:2909-2913) and must continue to express OspC in order to establish an infection in mammals (Stewart et al., *Infect. Immun.* 2006, 74:3547-3553, Tilly et al., *Infect. Immun.* 2006, 74:3554-3564). Therefore, the "window of effectiveness" of the OspC borreliacidal antibodies is increased significantly compared to OspA borreliacidal antibodies.

It has been shown that the OspC protein can induce protective borreliacidal antibodies (Rousselle et al., *J. Infect. Dis.* 1998, 178:733-741, Ikushima et al., *FEMS Immunol. Med. Microbiol.* 2000, 29:15-21), but some previous "mapping" studies have localized the epitopes to highly heterogeneous regions of the protein (Buckles et al., *Clin. Vacc. Immunol.* 2006, 13:1162-1165). Therefore, borreliacidal OspC antibodies raised against these regions would only provide antibody-mediated immunity against a small number of *Borrelia* spp. isolates. Lovrich et al. (*Clin. Diagn. Lab. Immunol.* 2005, 12:746-751) identified an OspC borreliacidal antibody epitope within the C-terminal 7 amino acids (OspC7) of the protein. Most significantly, the epitope is conserved among the pathogenic *Borrelia* spp. However, traditional laboratory *B. burgdorferi* ss isolates that express OspA (i.e., contain the ospA/ospB operon) cannot be manipulated in the laboratory to also induce significant levels of OspC borreliacidal antibodies without significantly impairing their ability to induce OspA borreliacidal antibodies. Moreover, vaccinating with killed traditional laboratory *B. burgdorferi* ss isolates that express OspA does not induce borreliacidal OspC antibodies (Schwan et al., 1995, *Proc. Natl. Acad. Sci. USA*, 92:2909-2913, Obonyo et al., 1999, *J. Clin. Microbiol.*, 37:2137-2141).

Callister et al., (U.S. Pat. Nos. 6,210,676 and 6,464,985, incorporated by reference herein) have suggested employing an immunogenic polypeptide fragment of OspC, alone or in combination with an OspA polypeptide, to prepare a vaccine to protect humans and other mammals against Lyme disease. Livey et al. (U.S. Pat. No. 6,872,550, incorporated by reference herein) also proposed a vaccine for immunizing against Lyme disease prepared from a combination of recombinant OspA, OspB, and OspC proteins. However, to date, no recombinant protein vaccine has been shown to be an improvement over the vaccines that are currently marketed. Therefore, there remains a longstanding need in the art for an improved vaccine to protect mammals, and especially canines, from Lyme disease.

The citation of any reference herein should not be construed as an admission that such reference is available as "prior art" to the instant application.

SUMMARY OF THE INVENTION

Accordingly, the present invention provides new immunogenic compositions that may be used in vaccines. In one aspect of the present invention, a vaccine protects against Lyme disease. In a particular embodiment of this type, the recipient of the vaccine is a canine. In another embodiment, the recipient of the vaccine is a domestic cat. Other domestic mammals may be protected by the vaccines and/or methods of the present invention such as horses and/or cattle. The present invention further provides combination vaccines for eliciting protective immunity against Lyme disease and other diseases, e.g., other canine infectious diseases. Methods of making and using the vaccines of the present invention are also provided.

A vaccine of the present invention comprises an immunologically effective amount of organisms of a first or a single strain (optionally inactivated) that expresses OspC antigen. The strain is one that, when grown under standard culture conditions, is killed in the presence of OspC-specific borreliacidal antibodies (complement is optionally required), including borreliacidal antibodies against the conserved epitope OspC7, elicited in an animal vaccinated by *B. burgdorferi* ss 50772 (ATCC No. PTA-439). In a particular embodiment of this type, the first or a single strain of *Borrelia* genospecies constitutively expresses the OspC antigen. In a more particular embodiment, the first strain is *B. burgdorferi* ss 50772 (ATCC No. PTA-439).

A vaccine composition of the present invention can further include an immunologically effective amount of inactivated organisms from one or more additional strains (which may be collectively labeled herein as the second strain), from a pathogenic *Borrelia* genospecies. In a particular embodiment the second strain exhibits OspA and OspB antigens.

Examples of appropriate second strains include one or more of the following: *B. burgdorferi* ss S-1-10 (ATCC No. PTA-1680), *B. burgdorferi* ss B-31 (ATCC No. 35210), *B. afzelii* (e.g., available as ATCC No. 51567) and *B. garinii* (e.g., available as ATCC Nos. 51383 and 51991), *B. burgdorferi* ss DK7, *B. burgdorferi* ss 61BV3, *B. burgdorferi* ss ZS7, *B. burgdorferi* ss Pka, *B. burgdorferi* ss IP1, IP2, IP3, *B. burgdorferi* ss HII, *B. burgdorferi* ss P1 F, *B. burgdorferi* ss Mil, *B. burgdorferi* ss 20006, *B. burgdorferi* ss 212, *B. burgdorferi* ss ESP1, *B. burgdorferi* ss Ne-56, *B. burgdorferi* ss Z136, *B. burgdorferi* ss ia, and/or any combinations thereof.

The vaccine composition broadly includes from about $1 \times 10^4$ to about $1 \times 10^{10}$ organisms per milliliter of each respective strain. In a particular embodiment, the vaccine includes from about $1 \times 10^6$ to about $5 \times 10^9$ organisms per milliliter of each respective strain. In another embodiment, the vaccine includes from about $1.0 \times 10^8$ to about $5 \times 10^8$ organisms per milliliter of the (or each) second strain and from about $5.0 \times 10^8$ to about $5 \times 10^9$ organisms per milliliter of the first strain.

The vaccine composition also can include a pharmaceutically acceptable adjuvant, e.g., such as, aluminum compounds (e.g., aluminum phosphate, aluminum hydroxide) metabolizable and non-metabolizable oils, block polymers, immune stimulating complexes, vitamins and minerals, and CARBOPOL® (e.g., CARBOPOL 941). In a particular embodiment the pharmaceutically acceptable adjuvant comprises a uniformly dispersed micron size oil droplets in water emulsion (e.g., as sold under the trademark Emulsigen®).

Optionally, the vaccine composition also includes a pharmaceutically acceptable immune stimulant, e.g., cytokines, growth factors, chemokines, supernatants from cell cultures of lymphocytes, monocytes, or cells from lymphoid organs, cell preparations and/or extracts from plants, bacteria or parasites, or mitogens.

The invention further provides for a method of immunizing a canine, or other mammal, against pathogenic *Borrelia* spp., specifically *B. burgdorferi* ss, comprising injecting the canine with an immunologically effective amount of the above described inventive vaccine. Such vaccines can include from about $1 \times 10^8$ to about $3 \times 10^9$ organisms of each respective strain, for example. Vaccines may be administered by a route such as: intramuscular injection, subcutaneous injection, intravenous injection, intradermal injection, oral administration, intranasal administration, and combinations thereof. In a particular embodiment, after vaccination, the immunized canine produces borreliacidal antibodies.

The invention further provides serum obtained from a vaccinated animal that contains borreliacidal antibodies that bind to *B. burgdorferi* ss OspC. Similarly, the invention provides for purified antibodies that bind to OspC. In a particular embodiment, the serum contains a significant proportion of OspC7-specific borreliacidal antibodies.

The invention further provides combination vaccines that include one or more strains of the *Borrelia* genospecies of the present invention in combination with one or more other canine pathogens and/or immunogens, including, e.g., immunogens for eliciting immunity to canine distemper virus; canine adenovirus; canine parvovirus; canine parainfluenza virus; canine coronavirus; canine influenza virus; and/or *Leptospira* serovars, e.g., *Leptospira kirschneri* serovar grippotyphosa, *Leptospira interrogans* serovar canicola, *Leptospira interrogans* serovar icterohaemorrhagiae, and/or *Leptospira interrogans* serovar pomona. Additional canine pathogens that can be added to a combination vaccine of the present invention include *Leishmania* organisms such as *Leishmania major* and *Leishmania infantum*; *Bordetella bronchiseptica*; a *Mycoplasma* species (e.g., *Mycoplasma cynos*); rabies virus; *anaplasma* organisms such as *anaplasma phagocytophilum* and *anaplasma platys*; and *Ehrlichia canis*.

These and other aspects of the present invention will be better appreciated by reference to the following Figures and the Detailed Description.

DETAILED DESCRIPTION OF THE INVENTION

Figure 1:
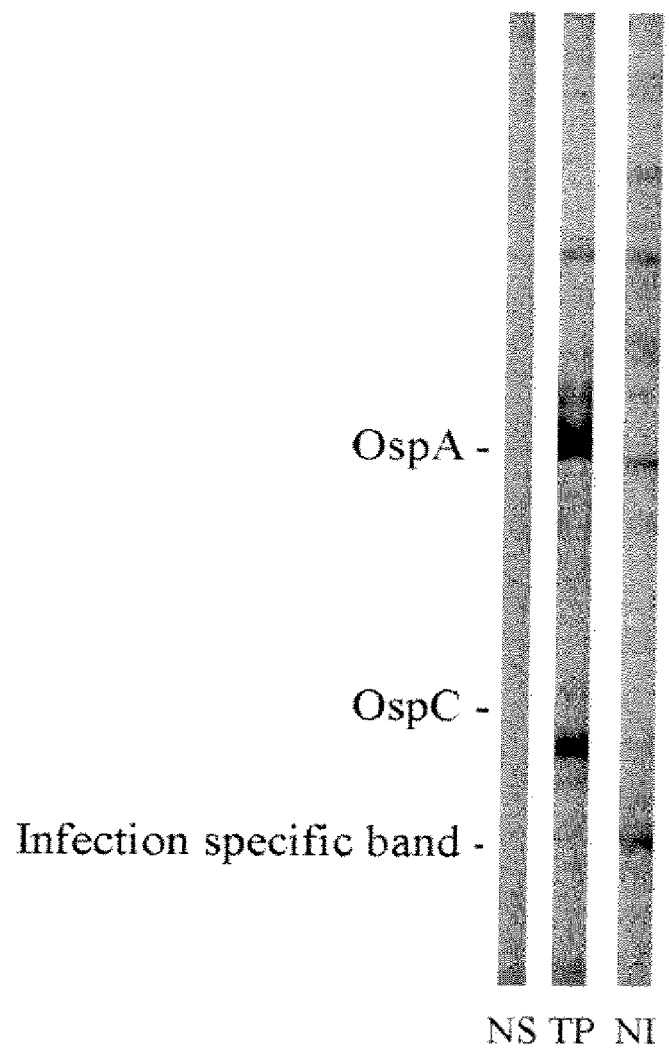
FIG. 1 is a Western blot of a normal dog serum control (NS) or sera from a dog after vaccination (study day 43) with the test product (TP) or after challenge (study day 134) with *B. burgdorferi* ss-infected ticks (NI). Note the presence of infection-specific antibodies against a protein with a molecular weight of approximately 20 kDa.

The present invention provides vaccine compositions that include an immunologically effective amount of organisms from one or more strains of a *Borrelia* genospecies that induce an effective borreliacidal antibody-mediated immunity in the recipient vaccinated animal. When organisms of such strains are grown under standard *Borrelia* genospecies growth conditions they are killed in the presence of OspC-specific antibodies, e.g., an antibody or antibodies elicited in an animal vaccinated with *B. burgdorferi* ss 50772 (ATCC No. PTA-439).

In one aspect of the present invention, the window of effectiveness of the antibodies induced by a vaccine of the present invention is increased significantly compared to conventional vaccines based solely on OspA borreliacidal antibodies. In another aspect, a vaccine of the present invention provides a better chance of stimulating a beneficial immunologic memory response, e.g., due to the expression of OspC in vivo, and/or an additional and/or enhanced protection against multiple pathogenic strains of *Borrelia* spp.

In one embodiment of the present invention, when the organisms of such strains are grown under standard *Borrelia* genospecies growth conditions, they constitutively express OspC antigen. In a particular embodiment of this type, when the organisms of such strains are grown under standard *Borrelia* genospecies growth conditions they are killed by a complement specific reaction. In yet another embodiment, a significant proportion of the OspC-specific borreliacidal antibodies in the sera induced by a vaccine comprising organisms of such strains are specific for the conserved epitope OspC7 and thereby, provide protection against multiple pathogenic *Borrelia* genospecies (e.g. *B. burgdorferi* ss, *B. afzelii*, and/or *B. garinii*). In still another embodiment, organisms of such strains exhibit no OspA or OspB antigen. In yet another embodiment, organisms of such strains have any two or more of these properties. In yet another embodiment, organisms of such strains have any three or more of these properties. In still another embodiment, organisms of such strains have any four or more of these properties. In a particular embodiment, organisms of such strains have all of these properties. One such particular strain is *B. burgdorferi* ss 50772 (ATCC No. PTA-439).

In an alternative embodiment, the inventive vaccine is a composition that includes both a first strain as described above and an effective amount of organisms of at least a second strain. The second strain is preferably from a pathogenic *Borrelia* genospecies that induces borreliacidal OspA antibodies when administered as a part of the inventive vaccine. One or more additional compatible vaccine genospecies can also be included therein. In addition, the vaccines of the present invention can include one or more other mammalian (e.g., canine) pathogens and/or immunogens.

In order to more fully appreciate the invention, the following definitions are provided.

The use of singular terms for convenience in description is in no way intended to be so limiting. Thus, for example, reference to a composition comprising "a polypeptide" includes reference to one or more of such polypeptides. In addition, reference to an "organism" includes reference to a plurality of such organisms, unless otherwise indicated.

As used herein the term "approximately" is used interchangeably with the term "about" and signifies that a value is within fifty percent of the indicated value i.e., a composition containing "approximately" $1 \times 10^{10}$ organisms per milliliter contains from $5 \times 10^9$ to $5 \times 10^{10}$ organisms per milliliter.

The term "genospecies," was first used and defined by G. Baranton et al., 1992, *International J. of Systematic Bacteriology* 42: 378-383, and is used herein in the same way that the term, "species" is employed in describing the taxonomy of non-*Borrelia* organisms.

"Standard growth conditions" for culturing *Borrelia* genospecies require growth at a temperature ranging from about 33° C. to about 35° C., in BSK (Barbour Stoenner Kelly) medium. BSK medium as described herein was prepared according to Callister et al. [*Detection of Borreliacidal Antibodies by Flow Cytometry*, Sections 11.5.1-11.5.12, *Current Protocols in Cytometry*, John Wiley and Sons, Inc. Supplement 26, (2003) hereby incorporated by reference herein in its entirety]. (BSK medium is also commercially available, e.g., from Sigma, St. Louis, Mo.).

As used herein "OspC7" is an immunodominant OspC borreliacidal antibody epitope located in a 7 amino acid region (Lovrich et al., 2005, *Clin. Diagn. Lab. Immunol.*, 12:746-751, incorporated by reference herein in its entirety) within the C-terminal 50 amino acids of OspC, as disclosed by Callister et al. (U.S. Pat. Nos. 6,210,676 B1 and 6,464,985 B1, which are incorporated by reference herein in their entireties) that is absolutely conserved among the known pathogenic *Borrelia* spp. This conservation is readily confirmed by a BLAST search of the codon segment encoding the 7 amino acid segment described by Lovrich et al. Such a search, when conducted on Oct. 9, 2006 generated a results list of 100 *Borrelia* species containing the above noted OspC 7-mer epitope coding segment.

An "OspC-specific borreliacidal antibody" is one that is found, e.g., in the serum of an animal vaccinated with *B. burgdorferi* ss 50772 (ATCC No. PTA-439), and is one that selectively binds to any epitope of the OspC antigen and kills the spirochetes dependent or independent of complement. An "OspC7-specific borreliacidal antibody" is one that is found, e.g., in the serum of an animal vaccinated with *B. burgdorferi* ss 50772 (ATCC No. PTA-439), and is one that selectively binds to the 7 C-terminal amino acids of OspC as described by Lovrich et al. [*Clin. Diagn. Lab. Immunol.*, 12:746-751, (2005), incorporated by reference herein in its entirety] and kills the spirochetes (generally by inducing a complement-mediated membrane attack complex). The specificity of OspC borreliacidal antibodies has been well-established. For example, OspC borreliacidal antibodies are detected commonly in Lyme disease sera by measuring the susceptibility of *B. burgdorferi* ss 50772 in a borreliacidal antibody test. Sera from human patients with closely-related illnesses only rarely (2%) contain cross-reactive antibodies that also kill strain 50772 (described in detail by Callister, et al., 1996, *Clinical and Diagnostic Laboratory Immunology* 3(4): 399-402). Moreover, a peptide ELISA that uses the OspC7 borreliacidal epitope accurately captures borreliacidal antibodies in Lyme disease sera, and sera from patients with other closely related illnesses only rarely (<2%) contain cross-reactive antibodies that also bind the OspC7 peptide (illustrated by FIGS. 4 and 5).

When a "significant proportion" of the OspC-specific borreliacidal antibodies in sera induced by a vaccine are specific for the conserved epitope OspC7, it means that there is a measurable reduction in the OspC-specific borreliacidal antibodies in the sera following the absorption of that sera with OspC7. It is preferably defined as at least a 2-fold reduction in the borreliacidal antibody titer of the sera detected by using *B. burgdorferi* ss 50772, and more preferably as a 2- to 4-fold, or greater reduction in the borreliacidal antibody titer of the sera following the absorption of that sera with OspC7.

A "complement specific reaction" is an antibody reaction that requires serum complement to be present in order for *Borrelia* spp. organism(s) to be killed by a borreliacidal antibody.

For the purposes of this invention, an "inactivated" *Borrelia burgdorferi* ss organism is an organism which is capable of eliciting an immune response in an animal, but is not capable of infecting the animal. The *Borrelia burgdorferi* ss isolates may be inactivated by an agent selected from the group consisting of binary ethyleneimine, formalin, beta-propiolactone, thimerosal, or heat. In a particular embodiment, the *Borrelia burgdorferi* ss isolates are inactivated by binary ethyleneimine.

The terms "adjuvant" and "immune stimulant" are used interchangeably herein, and are defined as one or more substances that cause stimulation of the immune system. In this context, an adjuvant is used to enhance an immune response to one or more vaccine antigens/isolates. An adjuvant may be administered to the target animal before, in combination with, or after the administration of the vaccine. Adjuvants of the present invention may be obtained from any of a number of sources including from natural sources, recombinant sources, and/or be chemically synthesized, etc. Examples of chemical compounds used as adjuvants include, but are not limited to aluminum compounds, metabolizable and non-metabolizable oils, block polymers, ISCOM's (immune stimulating complexes), vitamins and minerals (including but not limited to: vitamin E, vitamin A, selenium, and vitamin B12), Quil A (saponins), and polymers of acrylic acid cross-linked with polyalkenyl ethers or divinyl glycol e.g., CARBOPOL®. Additional examples of adjuvants, that sometimes have been referred to specifically as immune stimulants, include bacterial and fungal cell wall components (e.g., lipopolysaccarides, lipoproteins, glycoproteins, muramylpeptides, beta-1,3/1,6-glucans), various complex carbohydrates derived from plants (e.g., glycans, acemannan), various proteins and peptides derived from animals (e.g., hormones, cytokines, co-stimulatory factors), and novel nucleic acids derived from viruses and other sources (e.g., double stranded RNA, CpG). In addition, any number of combinations of the aforementioned substances may provide an adjuvant effect, and therefore, can form an adjuvant of the present invention. One preferred adjuvant is Emulsigen®.

*B. burgdorferi* ss 50772 (ATCC No. PTA-439) as stated in U.S. Pat. No. 6,210,676, and *B. burgdorferi* ss S-1-10 (ATCC No. PTA-1680) as stated in U.S. Pat. No. 6,316,005, were deposited with the American Type Culture Collection, University Boulevard Manassas (VA) 20110 on Jul. 30, 1999, and Apr. 11, 2000, respectively. The co-owners of the rights to the present invention individually hold the rights to these two aforementioned patents.

It is also to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting, since the scope of the present invention will be limited only by the appended claims and equivalents thereof.

Additional Vaccine Strains

Additional OspC Strains

In one aspect, the present invention provides the use of *B. burgdorferi* ss 50772 (ATCC No. PTA-439) in a vaccine that protects against Lyme disease, either alone, or in combination with other *Borrelia* genospecies strains. Notably, *B. burgdorferi* ss 50772 was initially rejected as a candidate for being useful in a vaccine because it was incorrectly reported that this strain did not express OspC (Anderson et al., 1996, *J. Clin. Microbiol.*, 34:524-529).

The present invention further provides unique and specific criteria to select/identify other such useful isolates for vaccines of the present invention. In particular, isolates can be selected/identified that are susceptible to being killed by OspC-specific antibodies, and preferably, for also possessing one or more, or all of the following attributes: (i) the susceptibility to being killed by OspC-specific antibodies through a complement specific reaction, (ii) the ability to induce OspC borreliacidal antibodies in a recipient vaccinated by that isolate; (iii) for a significant proportion of the OspC borreliacidal antibodies so induced to be specific for the conserved epitope within the C-terminal 7 amino acids (OspC7); (iv) lacking the capacity to express OspA and OspB; and/or (v) the ability to express OspC constitutively in vitro.

A. Suppression of OspA/B Expression and Enhancement of OspC Expression by Culture Conditions It has been shown by Obonyo et al. (*J. Clin. Microbiol.* 1999, 37:2137-2141) that OspA expression can be downregulated, and OspC expression can be upregulated over a five day period by co-culturing a normal pathogenic *Borrelia* spp. strain (strains JMNT and N40 of *B. burgdorferi* ss) with a tick cell line (*Ixodes scapularis* ISE6). The most pronounced effect was seen by culturing at 37° C. Thus, this method will convert one or more conventional pathogenic *Borrelia* strains into a form useful for a vaccine of the present invention.

B. Suppression of OspA/B Expression and Enhancement of OspC Expression by Mutation In a further embodiment, genetic manipulation of a *Borrelia* spp. strain that originally expresses OspA and OspB is employed to downregulate or to delete the genes that code for the expression of OspA and OspB that results in the upregulation of OspC expression. Any art-known method of genetic manipulation is contemplated to be employed for this purpose. For example, an inactivated analog of the OspA/OspB gene is introduced into a plurality of organisms of an available *Borrelia* spp. strain in the form of a *Borrelia* spp. compatible plasmid prepared with an antibiotic selection marker (see, e.g., Grimm et al., 2004, *Proc. Nat'l Acad. Sci.* 101(9):3142-3147 who report that OspC expression can be blocked in a *Borrelia* spp. by inserting OspC inactivation and complementation plasmids into a *B. burgdorferi* B31-A3 strain). Recombination events between the introduced plasmid and the naturally occurring plasmid carrying OspA/OspB will result in a certain number of successful recombinant *Borrelia* spp. organisms carrying a mutated OspA/OspB plasmid. Selection can be premised, for example, via a linked antibiotic resistance and growth in the presence of the corresponding antibiotic. *Borrelia* spp. organisms with selective elimination of OspA/OspB expression are contemplated to upregulate the expression of OspC.

In a further optional embodiment, one or more additional *B. burgdorferi* ss or *Borrelia* spp. organisms that express OspA, OspB, and/or one or more additional Osp antigens can be included in the vaccine composition as additional organisms.

Preferably, each respective inactivated organism is present in the vaccine in a concentration ranging from about $1 \times 10^4$ to about $1 \times 10^{10}$ organisms/mL. In particular, the vaccine is preferably administered to a canine in a dose of no less than $1.0 \times 10^8$ organisms/mL of *B. burgdorferi* ss S-1-10, and no less than $5.0 \times 10^8$ organisms/mL of *B. burgdorferi* ss 50772.

Additional OspA Strains

A second strain, providing the OspA antigen, can be a conventional pathogenic laboratory *B. burgdorferi* ss isolate (Barbour et al., 1985, *J. Clin. Microbiol.* 52:478-484) such as *B. burgdorferi* ss B-31 (ATCC No. 35210). A particular second organism is the exemplified *B. burgdorferi* ss S-1-10 strain (ATCC No. PTA-1680). Additional strains suitable for use as the second organism for vaccine compositions optimized for regions outside of North America include, e.g., the strains: *B. burgdorferi* ss B-31 (ATCC No. 35210), *B. afzelii* (e.g., available as ATCC No. 51567) and *B. garinii* (e.g., available as ATCC Nos. 51383 and 51991), as well as those listed in Table 1 below.

TABLE 1

| Strain | Country | Cultured from |
|---|---|---|
| *B. burgdorferi* ss DK7 [1] | Denmark | skin |
| *B. burgdorferi* ss 61BV3 [1] | Germany | skin |

TABLE 1-continued

| Strain | Country | Cultured from |
|---|---|---|
| *B. burgdorferi* ss ZS7 [1] | Switzerland | tick |
| *B. burgdorferi* ss Pka [1] | Germany | tick |
| *B. burgdorferi* ss IP1, IP2, IP3 [1] | France | CSF |
| *B. burgdorferi* ss HII [1] | Italy | blood |
| *B. burgdorferi* ss P1F [1] | Switzerland | synovia |
| *B. burgdorferi* ss Mil [1] | Slovakia | tick |
| *B. burgdorferi* ss 20006 [1] | France | tick |
| *B. burgdorferi* ss 212 [1] | France | tick |
| *B. burgdorferi* ss ESP1 [1] | Spain | tick |
| *B. burgdorferi* ss Ne-56 [1] | Switzerland | tick |
| *B. burgdorferi* ss Z136 [1] | Germany | tick |
| *B. burgdorferi* ss ia [2] | Finland | CSF |

[1] Lagal et al., J. Clin. Microbiol, 2003, 41: 5059-5065.
[2] Heikkila et al, J. Clin. Microbiol. 2002, 40: 1174-1180.

The vaccine composition can include a pharmaceutically acceptable adjuvant. "Adjuvants" are agents that nonspecifically increase an immune response to a particular antigen, thus reducing the quantity of antigen necessary in any given vaccine, and/or the frequency of injection necessary in order to generate an adequate immune response to the antigen of interest. Suitable adjuvants for the vaccination of animals include, but are not limited to, Adjuvant 65 (containing peanut oil, mannide monooleate and aluminum monostearate); Freund's complete or incomplete adjuvant; mineral gels, such as aluminum hydroxide, aluminum phosphate, and alum; surfactants, such as hexadecylamine, octadecylamine, lysolecithin, dimethyldioctadecylammonium bromide, N,N-dioctadecyl-N',N'-bis (2-hydroxymethyl)propanediamine, methoxyhexadecylglycerol, and pluronic polyols; polyanions, such as pyran, dextran sulfate, poly IC, polyacrylic acid, and CARBOPOL® (e.g., CARBOPOL 941); peptides, such as muramyl dipeptide, dimethylglycine and tuftsin; and oil emulsions. Information concerning adjuvants is disclosed, e.g., in the series by P. Tijssen [*Practice and Theory of Enzyme Immunoassays*, 3rd Edition, 1987, Elsevier, New York, incorporated by reference herein].

Optionally, the vaccine composition can further include a pharmaceutically acceptable immune stimulant, such as bacterial and/or fungal cell wall components (e.g., lipopolysaccarides, lipoproteins, glycoproteins, muramylpeptides), various complex carbohydrates derived from plants (e.g., glycans, acemannan), various proteins and peptides derived from animals (e.g., hormones, cytokines, co-stimulatory factors), and novel nucleic acids derived from viruses and/or other sources (e.g., double stranded RNA, CpG).

The vaccine composition is readily administered by any standard route including intravenous, intramuscular, subcutaneous, oral, intranasal, intradermal, and/or intraperitoneal vaccination. The artisan will appreciate that the vaccine composition is preferably formulated appropriately for each type of recipient animal and route of administration.

Thus, the present invention also provides methods of immunizing a canine against *B. burgdorferi* ss and other *Borrelia* spp. One such method comprises injecting a canine with an immunologically effective amount of a vaccine of the present invention, so that the canine produces appropriate OspA and OspC borreliacidal antibodies.

In one embodiment, the subcutaneous administration of the present invention results in the production of high concentrations of OspA and OspC borreliacidal antibodies including borreliacidal antibodies specific for OspC7. In another embodiment, the present invention provides a vaccine that comprises a specific, minimum amount of each *B. burgdorferi* ss strain that is effective against harmful *Borrelia* spp. In another embodiment, a vaccine of the present invention is effective for the prevention of *B. burgdorferi* ss and other pathogenic *Borrelia* spp. infections in dogs. In a particular embodiment, the vaccine comprises a safe and immunologically effective combination of two *B. burgdorferi* ss strains of the present invention and a pharmaceutically acceptable adjuvant.

The present invention discloses that a vaccine comprising a specific minimal amount of two *B. burgdorferi* ss isolates protects dogs from *Borrelia* spp. following tick challenge. The present invention further discloses a vaccine that elicits specific minimal amounts of *B. burgdorferi* ss-specific OspA and *Borrelia* spp.-specific OspC borreliacidal antibodies in vaccinated dogs. The vaccines of the present invention also may be administered with an acceptable immune stimulant and/or adjuvant.

EXAMPLES

The following examples serve to provide further appreciation of the invention but are not meant in any way to restrict the effective scope of the invention.

Example 1

Vaccination with Recombinant OSPA

A. Materials and Methods
Animals:
Five- to 10-week old LVG hamsters were obtained from Charles River Breeding Laboratories, Inc. (Wilmington, Mass.). Hamsters were housed three or four per cage at an ambient temperature of 21° C. and provided with food and water ad libitum.

Vaccination of Hamsters and Collection of Serum:
Hamsters were vaccinated subcutaneously in the back of the neck with 0.5 mL of a commercially available recombinant OspA (rOspA) vaccine, RECOMBITEK® Lyme, (Merial Limited, Duluth, Ga.), and given a booster three weeks after the primary vaccination. At 3, 7, 9, and 15 weeks after the primary vaccination, groups of five hamsters each were mildly anesthetized by inhalation of ether contained in a nose-and-mouth cup and bled by intracardiac puncture. The blood was allowed to clot, and the serum was separated and stored at −70° C. until use. In addition, hamster sera from three unvaccinated hamsters were pooled and used as a normal serum control. As an additional control, 20 hamsters were vaccinated in both hind thighs with 0.25 mL of a commercially available whole cell canine Lyme disease vaccine (Galaxy, Solvay Animal Health, Inc., Mendota Heights, Minn., now Schering-Plough Animal Health, Elkhorn, Nebr.) that contained *B. burgdorferi* ss S-1-10. The animals were given a booster, and sera were collected as described above.

Preparation of BSK Medium:
Barbour-Stoenner-Kelly (BSK) broth medium was used for in vitro cultivation of *B. burgdorferi* and was the primary substrate used in the borreliacidal antibody test and in methods described throughout the present application. BSK medium was prepared as described by Callister et al., [*Detection of Borreliacidal Antibodies by Flow Cytometry*, Section 11.5.1-11.5.12, *Current Protocols in Cytometry*, John Wiley and Sons, Inc., Supplement 26, (2003) hereby incorporated by reference herein in its entirety. In brief, the BSK medium was prepared by the following method.
Materials:
HEPES (Sigma)
Neopeptone (Difco)
Sodium citrate (Sigma)
Glucose (Sigma)
Sodium bicarbonate (Sigma)
TC yeastolate (Difco)
Pyruvic acid (Sigma)
N-acetyl glucosamine (Sigma)

Bovine serum albumin (Sigma)
Gelatin (microbiological grade; Difco)
5N NaOH
10× Connaught Medical Research Laboratories (CMRL) 1066
(MP Biomedicals) or Roswell Park Memorial Institute (RPMI) 1640 medium
(Sigma) with L-glutamine and without sodium bicarbonate
Rabbit serum (Life Technologies), heat-inactivated 45 min at 56° C.
56° C. water bath
Positive-pressure pump
Millipore filter manifold
Prefilter (124 mm)
0.2-, 0.45-, and 0.8-μm filters (142-mm diameter)
0.2-μm bell filters
Sterile 100-ml containers
Dark-field microscope
Preparation of Bsk Medium
1. The following were combined in a 2-liter flask, with from 2 to 4 hours of mixing. 900 mL Mini-Q double-filtered or deionized distilled water:
6.0 g HEPES
5.0 g neopeptone
0.7 g sodium citrate
5.0 g glucose
2.2 g sodium bicarbonate
2.5 g TC yeastolate
0.8 g pyruvic acid
0.4 g N-acetyl glucosamine
50 g bovine serum albumin (fraction V)
2. The components were slowly mixed using the slowest stir plate setting because vigorous stirring may result in breakdown products toxic to *B. burgdorferi*.
3. While the BSK components were mixing, the gelatin solution was prepared as follows: in a 500-mL flask, 200 mL Milli-Q double-filtered or deionized distilled water and 14 g gelatin were combined and heated on a medium setting with stirring to dissolve. The solution was then autoclaved for 15 min at 121° C., and then placed in a 56° C. water bath.
4. When BSK components were dissolved completely, the solution was adjusted to pH 7.5 with 5N NaOH.
5. The 200 mL gelatin solution, 100 mL 10×CMRL 1066 medium, and 64 mL heat-inactivated rabbit serum (45 min at 56° C.) were then combined with the other BSK components and thoroughly mixed.
BSK Medium Sterilized
6. Using the positive-pressure pump, BSK medium was pumped through the Millipore filter manifold loaded with a 124-mm prefilter and 142-mm 0.2-, 0.45-, and 0.8-μm pore diameter filters stacked from smallest (bottom) to largest (top) pore size. [The BSK medium cannot be sterilized by autoclaving. Pre-filtration was necessary to remove large particulates prior to filter sterilization.]
7. The BSK medium was then filter-sterilized into a sterile container using the positive-pressure pump and a sterile 0.2-μm bell filter.
Sterility Confirmed
8. A 1-mL aliquot of sterile BSK was aseptically removed and transferred to a sterile 1.5-mL microcentrifuge tube, and incubated overnight at 35° C. The remaining filter-sterilized BSK was stored at 4° C.
9. Following the incubation, the sterile BSK was examined using dark-field microscopy to confirm sterility.
10. The sterile BSK was then transferred into sterile storage containers. [Headspace was kept to a minimum when filling the storage containers in order to reduce the oxidation of the sterile BSK medium.]

Quality Control Of Barbour-Stoenner-Kelly (BSK) Medium

Before using BSK medium, it is important to make sure that BSK supports the growth of small numbers of *Borrelia* spp. and that the viable spirochetes grow without clumping. A highly variable component of BSK medium is bovine serum albumin (BSA). The quality control protocol employed herein utilized test cultures to incubate and inspect resulting cultures, as described in detail by Callister et al., 2003, Id.

Detection of OspA Borreliacidal Antibodies:

OspA borreliacidal antibodies were detected using a flow cytometric procedure and *B. burgdorferi* ss S-1-10 (Callister et al., *Arch. Intern. Med.* 1994, 154:1625-1632). A fresh culture of the spirochetes was diluted with fresh BSK to a concentration of approximately $5 \times 10^6$ spirochetes/mL. Concomitantly, serum samples were diluted 1:40 with fresh BSK and sterilized by passage through a 0.2 micron (μm) pore-size microcentrifuge filter. A 200 μL aliquot was then transferred to a sterile 1.5 mL screw-cap microcentrifuge tube and serially diluted in BSK from 1:80 to 1:20,480. Serum samples were heat-inactivated at 56° C. for 10 min, and a 100 μL aliquot of the spirochete suspension ($5 \times 10^5$ spirochetes) and 10 μL of sterile guinea pig complement (Sigma) were added. The assays were mixed thoroughly and incubated for 16-24 hours at 35° C.

Following incubation, 100 μL of each assay suspension was transferred to a polypropylene tube containing 400 μL of PBS and 1 μg/mL acridine orange. A FACScan flow cytometer (Becton Dickinson Immunocytometry Systems, San Jose, Calif.) was then used to detect borreliacidal activity. Spirochetes were isolated by gating (CellQuest software, Becton Dickinson) and analyzed for 1-2 min with the flow rate set at low. The OspA borreliacidal antibodies were detected indirectly by monitoring the increased fluorescence intensity that occurs when the acridine orange intercalates into blebbed, non-viable spirochetes. A $\geq 13\%$ shift in the mean fluorescence intensity compared to a normal serum control was considered positive (Callister et al., *Clin. Diagn. Lab. Immunol.* 2002, 9:908-912). The presence of blebbed, non-motile *B. burgdorferi* was then confirmed by darkfield microscopy. A positive control was included with each assay, and identical reactivity (+/– one dilution) from run to run was required to minimize interassay variability. In addition, serum samples collected from each dog were assayed concurrently.

B. Results

Vaccination with the rOspA vaccine induced only minimal amounts (mean titer<61) of OspA borreliacidal antibodies after 7 weeks that were not detected after 15 weeks (Table 2). In contrast, hamsters vaccinated with the canine vaccine that contained a typical (Barbour et al., *J. Infect. Dis.* 1985, 152-478-484) *B. burgdorferi* ss strain (S-1-10) induced high levels of borreliacidal OspA antibodies that peaked at week 7 (titer>2560) and remained elevated for the duration of the study.

TABLE 2

Mean titer[a] of OspA borreliacidal antibodies[b] after vaccination with rOspA or GALAXY ™ (S-1-10) canine Lyme disease vaccines.

| Vaccine | Week 3 | Week 7 | Week 9 | Week 15 |
|---|---|---|---|---|
| rOspA | 9 | 61 | 4 | ND[c] |
| S-1-10 | 1470 | >2560 | 970 | 735 |

[a]Reciprocal dilution.
[b]Detected by using *B. burgdorferi* ss S-1-10.
[c]ND = None detected.

Therefore, the canine recombinant OspA vaccine fails to elicit significant titers of OspA borreliacidal antibodies in hamsters.

Example 2

Vaccination with Recombinant OSPC

A. Materials and Methods

Animals:

Five- to 10-week old LVG hamsters were obtained from Charles River Breeding Laboratories, Inc. (Wilmington, Mass.). Hamsters were housed three or four per cage at an ambient temperature of 21° C. and provided with food and water ad libitum.

Preparation of Recombinant ("r") OspC Vaccine rOspC was recovered from *E. coli* JM109 containing pX3-22 as described previously (Rousselle et al., *J. Infect. Dis.* 1998, 178:733-741). Briefly, the *E. coli* was cultured at 37° C. in 2×TY broth containing ampicillin, and isopropyl-β-d-galactopyranoside (IPTG) (0.1 mM) was added during the exponential growth phase. Cells were pelleted by centrifugation, resuspended in phosphate buffered saline (PBS), and lysed by sonication. Triton X-100 (1% vol/vol) was added, and the lysate was centrifuged at 10,000×g for 5 min. The sonicated *E. coli* cells were then pelleted by centrifugation, and the supernatant was passed over a column containing SoftLink resin (Promega) that bound the OspC via a biotinylated purification tag on the amino terminus. The bound OspC was then eluted with a purification buffer that also contained 5 mM biotin (Sigma).

Vaccination of Hamsters and Collection of Serum:

Hamsters were vaccinated subcutaneously in the back of the neck with 0.1 mL of Freund's complete adjuvant that contained 75 μg of rOspC and then given a booster of 75 μg of rOspC in 0.1 mL of Freund's incomplete adjuvant three weeks after the primary vaccination. At 5 weeks after the primary vaccination, the hamsters were mildly anesthetized by inhalation of ether contained in a nose-and-mouth cup and bled by intracardiac puncture. The blood was allowed to clot, and the serum was separated and stored at −70° C. until use. In addition, hamster sera from three normal hamsters were pooled and used as a normal serum control.

Detection of OspC Antibodies:

rOspC was diluted to 1000 ng/mL in coating buffer (0.015 M $Na_2CO_3$, 0.035 M $NaHCO_3$, pH 9.6) and 100 μL amounts were added to individual flat-bottomed amine-binding microtiter wells (Costar, Cambridge, Mass.). Microtiter plates were incubated overnight at 4° C. After incubation, plates were washed 3 times with PBS (pH 7.2) and blocked with PBS containing 0.05% TWEEN 20 (Sigma) and 1% bovine serum albumin (Sigma) for 1 hour at room temperature with shaking. After blocking, plates were washed again with PBS. Subsequently, 100 μL amounts of hamster serum serially diluted from 1:80 to 1:20,480 in PBS/Tween was added to individual wells, and the plates were incubated for 1 hour at room temperature. Following incubation, plates were washed three times with PBS, 100 μL of anti-hamster IgG horseradish peroxidase conjugate (Organon Teknika Cappel) diluted 1:3000 in PBS/Tween was added to each well, and the plates were re-incubated at room temperature for 1 hour. Plates were then washed 3 times with PBS and 100 μL of o-phenylenediamine phosphate (0.4 mg/ml; Sigma) was added to each well and allowed to incubate at room temperature for 30 min. Reactions were stopped by adding 100 μL of 1 N $H_2SO_4$ and absorbances at 490 nm (model EL 311; Bio-Tek Inc. Winooski, Vt.) were immediately determined.

Detection of OspC Borreliacidal Antibodies:

OspC borreliacidal antibodies were detected as described above (Example 1), except B. burgdorferi ss 50772 was used.

B. Results

Vaccination with the rOspC vaccine induced high levels of OspC antibodies detected by the ELISA (Table 3, infra), but only a low level (titer 80) of borreliacidal activity was present. The vaccination with rOspC had therefore induced high concentrations of OspC antibodies, but the response was comprised almost entirely of antibodies (eg. opsonizing) that would not provide protection against infection. This was especially significant when one considered the 75 µg concentration of proteins in the B. burgdorferi ss 50772 vaccine was calculated without accounting for the presence of numerous additional non-OspC proteins. The collective results (Examples 1 and 2) therefore confirmed previous findings (Straubinger et al. Vaccine 2003, 20:181-193) that recombinant Osps stimulated significantly less amounts of borreliacidal antibodies than intact B. burgdorferi ss.

TABLE 3

Mean titer[a] of antibodies detected by OspC ELISA or OspC borreliacidal antibody test[b] after vaccination with rOspC.

| Sample | Antibody titer detected by:. | |
|---|---|---|
| | OspC ELISA | OspC borreliacidal antibody test |
| Normal | ND[c] | ND |
| rOspC | 10240 | 80 |

[a]Reciprocal dilution of pooled serum from 5 hamsters.
[b]Detected by using B. burgdorferi ss 50772
[c]ND = None detected.

Therefore, the canine recombinant OspC vaccine fails to elicit significant titers of OspC borreliacidal antibodies in hamsters.

Example 3

Vaccination with B. burgdorferi ss Isolate S-1-10

A. Materials and Methods

Organism:

B. burgdorferi ss S-1-10 is a typical pathogenic strain generally indistinguishable from B. burgdorferi ss B31 (Barbour et al., J. Infect. Dis., 1985, 152:478-484). The isolate was originally recovered by Dr. Steven M. Callister, Gundersen Lutheran Medical Foundation, La Crosse, Wis., from the kidney of a white-footed mouse, Peromyscus leucopus, captured February 1988 from a site near La Crosse, Wis., and was licensed by Solvay Animal Health for incorporation into a canine Lyme disease vaccine. The subsequent commercial product (GALAXY™ Lyme) was acquired by Schering Plough Animal Health on Apr. 17, 1997. The organism expresses OspA, OspB, and OspC. However, as is typical of infectious B. burgdorferi ss isolates, significantly higher concentrations of OspA and OspB are produced when the spirochetes are cultured in laboratory BSK medium. It has been shown that the expression of OspC can be maximized by incubation at 35° C. (Schwan, Biochem. Soc. Trans. 2003, 31:108-112).

Animals

Eight-week-old beagle puppies (Ridglan Farms, Mount Horeb, Wis.) were housed communally, and food and water was available ad libitum. The experiment was reviewed and approved by the Schering Plough Animal Health Animal Care and Use Committee (IACUC).

Preparation of B. burgdorferi ss S-1-10 Vaccine:

A fresh culture of B. burgdorferi ss S-1-10 that had reached logarithmic growth phase by incubation in BSK at 35° C. was inactivated by adding binary ethylenimine (BEI) to a final concentration of 10 mM and incubating for an additional 48 hours. After inactivation, the BEI was neutralized by adding sterile sodium thiosulfate and incubating at 35° C. for 6 to 12 hours. The spirochetes were then pelleted by centrifugation and resuspended in sterile balanced salt solution containing $\leq$30 µg of gentamicin/mL and $\leq$30 units of nystatin/mL. The spirochetes were then blended with 5% Emulsigen® (MVP Laboratories, Inc.) and 1% HEPES so that a 1.0 mL dose contained $\leq 2.5 \times 10^7$ spirochetes.

Vaccination and Collection of Serum:

Dogs were vaccinated subcutaneously in the neck with a 1 mL dose of the S-1-10 vaccine and boosted with an additional 1 mL dose after 21 days. Whole blood was collected immediately prior to the booster vaccination (study day 21) and at study days 28, 35, 47, 83, and 113 by venipuncture of the jugular vein. The serum was separated by centrifugation and stored at -20° C. until tested.

Detection of Borreliacidal Antibodies:

OspA and OspC borreliacidal antibodies were detected by flow cytometry employing B. burgdorferi ss S-1-10 and 50772, as described above in Examples 1 and 2.

B. Results

Vaccination with B. burgdorferi ss S-1-10 reliably induced high levels of borreliacidal OspA antibodies that were detectable at study day 21, peaked at study day 28, and remained detectable at study day 113 (Table 4, infra). In contrast, OspC borreliacidal antibodies were not detected (titer less than 1:80). Thus, the conventional B. burgdorferi ss strain failed to induce the production of OspC borreliacidal antibodies despite maximizing the OspC expression by incubating the spirochetes at 35° C.

TABLE 4

Mean titers[a] (n = 8) of OspA or OspC borreliacidal antibodies after vaccination with B. burgdorferi ss S-1-10.

| Borreliacidal Antibody | Day 21 | Day 28 | Day 35 | Day 47 | Day 83 | Day 113 |
|---|---|---|---|---|---|---|
| OspA[b] | 202 | 9481 | 9481 | 4740 | 1613 | 1382 |
| OspC[c] | ND[d] | ND | ND | ND | ND | ND |

[a]Reciprocal dilution.
[b]Detected by using B. burgdorferi ss S-1-10.
[c]Detected by using B. burgdorferi ss 50772.
[d]ND = None detected.

Therefore, a vaccine employing B. burgdorferi ss isolate S-1-10 failed to elicit a significant titer of OspC borreliacidal antibodies.

Example 4

Vaccination with B. burgdorferi ss Isolate 50772

A. Materials and Methods

Organism:

B. burgdorferi ss 50772 is a unique ospA-/ospB-strain originally reported by Anderson et al., J. of Clin. Microbiol., 1996, 34:524-529, who failed to identify it as expressing OspC antigen. The 50772 strain is described by U.S. Pat. No. 6,464,985, incorporated herein by reference in its entirety, as expressing OspC antigen, and this strain is reported by that U.S. patent as deposited with the ATCC as No. PTA-439.

Animals:

Eight-week-old beagle puppies (Ridglan Farms, Mount Horeb, Wis.) were housed communally, and food and water was available ad libitum. The experiment was reviewed and approved by the Schering Plough Animal Health Animal Care and Use Committee (IACUC).

Preparation of B. burgdorferi ss 50772 Vaccine:

B. burgdorferi ss 50772 vaccine was prepared as described above in Example 3.

Vaccination and Collection of Serum:

Dogs were vaccinated subcutaneously in the neck with a 1 mL dose of the 50772 vaccine and boosted with an additional 1 mL dose after 21 days. Whole blood was collected immediately prior to the booster vaccination (study day 21) and at study days 28, 35, 47, 83, and 113 by venipuncture of the jugular vein. The serum was separated by centrifugation and stored at −20° C. until tested.

Detection of Borreliacidal Antibodies:

OspC borreliacidal antibodies were detected by flow cytometry employing B. burgdorferi ss 50772 as described above in Examples 1 and 2.

B. Results

Vaccination with B. burgdorferi ss 50772 reliably induced high levels of borreliacidal OspC antibodies that peaked at study day 35 and remained detectable at study day 113 (Table 5, infra). Thus, in contrast to vaccinations with rOspC or a traditional B. burgdorferi ss isolate (S-1-10), vaccination with the unique B. burgdorferi ss strain 50772 induced significant levels of OspC borreliacidal antibodies.

TABLE 5

Mean Titers[a] (n = 8) of OspC Borreliacidal Antibodies[b] After Vaccination with B. burgdorferi ss 50772.

| Day 21 | Day 28 | Day 35 | Day 47 | Day 83 | Day 113 |
|---|---|---|---|---|---|
| ND[c] | 5530 | 1097 | 435 | 274 | 202 |

[a]Reciprocal dilution.
[b]Detected by using B. burgdorferi ss 50772.
[c]ND = None detected.

Therefore, a vaccine comprising the B. burgdorferi ss isolate 50772 induces high concentrations of OspC borreliacidal antibodies.

Example 5

Preparation of a Vaccine Comprising B. burgdorferi ss Isolates S-1-10 and 50772

A. Materials and Methods

Growth:

Frozen stock cultures of B. burgdorferi ss S-1-10 and B. burgdorferi ss 50772 were cultured under standard conditions, i.e., the stock cultures were grown at 33±2° C. and 35±2° C., respectively, in individual screw cap culture tubes containing 5 to 17 mL of BSK (Barbour Stoenner Kelly) medium [prepared according to Callister et al., 1990, *J. of Clinical Microbiology* 28: 363-365, hereby incorporated by reference in its entirety herein] under an atmosphere of air enriched with 5% $CO_2$. After reaching logarithmic growth, the cultures were used to inoculate 150 to 200 mL of fresh BSK medium, which were next incubated until the cultures reached logarithmic growth. The resultant suspensions were then used to inoculate 5 to 10 liters of fresh BSK contained in 10 to 20 liter jugs (production culture) prior to an additional incubation, as described above.

Inactivation:

The spirochetes in the production cultures were inactivated by adding BEI to a concentration of 10 mM and incubating with slow stirring for 24 to 48 hours. After inactivating the spirochetes, the BEI was neutralized by adding 10.6 mL of sterile 3.015M sodium thiosulfate to each liter of BSK/spirochete suspension and incubating with slow stirring for 6 to 12 hours.

Concentration and Blending:

Inactivated spirochetes were pelleted by centrifugation and resuspended in a sterile balanced salt solution containing 30.0 µg/mL of gentamicin and 30 units/mL of nystatin. The test vaccine was blended with 5% Emulsigen® (MVP Laboratories, Inc.) and filled in 2.0 mL glass vials so each dose (1.0 mL) contained ≧2.5×10$^7$ organisms/mL of B. burgdorferi ss S-1-10, ≧5.0×10$^8$ organisms/mL of B. burgdorferi ss 50772, 1% HEPES, 29 µg/mL gentamicin, and 29 units/mL nystatin.

Example 6

Safety and Efficacy of a Vaccine Comprising B. burgdorferi ss Isolates S-1-10 and 50772

A. Materials and Methods

Animals:

Eight-week-old beagle puppies (Ridglan Farms, Mount Horeb, Wis.) were housed individually or communally, and food and water was available ad libitum. The experiment was reviewed and approved by the Schering Plough Animal Health Animal Care and Use Committee (IACUC).

Vaccination and Collection of Sera:

Dogs were vaccinated subcutaneously in the neck with a 1 mL dose of the vaccine and boosted with an additional 1 mL dose after 21 days. Whole blood was collected prior to the initial (study day −3) and booster vaccination (study day 21) and also on study days 28, 35, 43, 78, 106, 134, 162, and 197 by venipuncture of the jugular vein. The serum was separated by centrifugation and stored at −20° C. until tested.

Post-Vaccination Observations:

After each vaccination, injection sites were palpated daily until no reaction could be felt, and rectal temperatures were recorded 4-6 hours post-vaccination and on days 1-3 post-vaccination.

Tick Challenge:

Three weeks after the second vaccination, dogs were shaved on the right side of the thoracic cavity, and 10 female and 10 male B. burgdorferi ss-infected I. scapularis ticks were placed in a rubber cup that was secured to the shaved area with tape and bandage wrap. The ticks were allowed to feed for 7 days.

Detection of B. burgdorferi ss in Ticks:

The tick mouthparts were removed by scalpel, and the midguts were teased and smeared onto glass slides and allowed to dry overnight at room temperature. After drying, the slides were fixed in acetone for 8-10 min and air-dried. Species-specific mouse OspA monoclonal antibody H5332 was diluted 1:40 in PBS (pH 7.2) and overlaid with goat anti-mouse fluorescein isothiocyanate-labeled immunoglobulin G antibody diluted 1:500 in PBS. After incubation, slides were rinsed with PBS, air-dried, and examined by fluorescence microscopy. Each slide was examined independently by two experienced microbiologists.

Blood Samples:

Whole blood was collected in serum separation transport (SST) tubes on study days 78, 106, 134, 162, and 197, and the serum was separated and stored at −20° C. until tested.

Removal of OspA Antibodies:

Recombinant (r)OspA was recovered from *Escherichia coli* ("*E. coli*") DH5α expressing OspA-glutathione-S-transferase fusion protein as described previously (Callister et al., *J. Infect. Dis.* 1993, 167:158-164). Briefly, the *E. coli* was cultured at 37° C. in 2×TY broth containing ampicillin, and isopropyl-β-d-galactopyranoside ("IPTG") (0.1 mM) was added during the exponential growth phase. Cells were pelleted by centrifugation, resuspended in phosphate buffered saline ("PBS"), and lysed by sonication. Triton X-100 (1% vol/vol) was added, and the lysate was centrifuged at 10,000×g for 5 minutes (min.). The supernatant containing the fusion protein was then passed over a glutathione-Sepharose 4B column (Pharmacia), and the recombinant OspA was eluted with 50 mM Tris-Cl (pH 8.0) plus 5 mM reduced glutathione and resuspended in purification buffer (50 mM Tris [pH 8], 50 mM NaCl, 2 mM EDTA, 0.1% Triton X-100).

The rOspA fusion protein was then bound to Sepharose 4B by cyanogen bromide (CNBr) activation. Specifically, 0.8 g of CNBr-activated Sepharose 4B (Pharmacia) was washed with coupling buffer (0.1 M $NaHCO_3$-0.5 M NaCl, pH 8.3), a 2 mg amount of OspA in coupling buffer was added to the gel, and the mixture was gently shaken at room temperature for 2 hours. After the gel was washed twice with coupling buffer, 4 mL of ethanolamine (pH 9) was added, and the gel was incubated for 2 hours to block unbound sites. The gel was washed three times with 50 mL of 0.1 M sodium acetate-0.5 M NaCl (pH 4.0) and then equilibrated in PBS. A 1 mL sample of immune serum diluted ten-fold in PBS was passed over the column four times.

Removal of OspC Antibodies:

rOspC was recovered from *E. coli* JM109 containing pX3-22 as described previously (Rousselle et al., *J. Infect. Dis.* 1998, 178:733-741). Production of the recombinant protein was induced as described for rOspA above. The sonicated *E. coli* cells were then pelleted by centrifugation, and the supernatant was passed over a column containing SoftLink resin (Promega) that bound the OspC via a biotinylated purification tag on the amino-terminus. The bound OspC was then eluted with a purification buffer that also contained 5 mM biotin (Sigma).

A 1 mL volume of Tetralink tetrameric avidin resin (Promega) was then washed, suspended in 40 mL of PBS, and loaded onto a 10-mm by 70-mm polypropylene column. A 0.5 mg amount of dialyzed rOspC in a 1 mL volume of PBS was passed over the column and binding was confirmed by protein assay (Bio-Rad). A 1 mL volume of immune serum diluted ten-fold in PBS was passed over the column four times.

Removal of OspC7-Specific Antibodies:

A fusion protein containing the 7 C-terminal amino acids of OspC (OspC7) was recovered from *E. coli* JM109 containing pXT7 as described previously (Lovrich et al., *Clin. Diagn. Lab. Immunol.* 2005, 12:746-751, incorporated by reference herein in its entirety). Production of the recombinant protein was induced as described for rOspA above. The sonicated *E. coli* cells were then pelleted by centrifugation, and the supernatant was passed over a column containing SoftLink resin (Promega) that bound the OspC7 via a biotinylated purification tag on the amino-terminus. The bound OspC7 was then eluted with a purification buffer that also contained 5 mM biotin (Sigma). A 1 mL volume of Tetralink tetrameric avidin resin (Promega) was then washed, suspended in 40 mL of PBS, and loaded onto a 10-mm by 70-mm polypropylene column. A 0.5 mg amount of dialyzed rOspC in a 1 mL volume of PBS was passed over the column and binding was confirmed by protein assay (Bio-Rad). A 1 mL volume of immune serum diluted ten-fold in PBS was passed over the column four times.

Detection of Borreliacidal Antibodies:

OspA and OspC borreliacidal antibodies were detected by flow cytometry employing *B. burgdorferi* ss S-1-10 and 50772 as described above in Examples 1 and 2.

Skin Biopsies:

Skin biopsies were taken from sites adjacent to tick attachment on study days 78, 106, 134, 162, and 197 with a disposable 4 mm puncture device. The biopsies were placed into separate tubes containing 9 mL of BSK (Callister et. al, *J. Clin. Microbiol.* 1990, 28:363-365) supplemented with gelatin (BSK+G), 40-50 micrograms (μg)/mL rifampin, and 8 μg/mL kanamycin. Cultures were incubated at 35±2° C. for 3 weeks and examined weekly by dark-field microscopy for spirochetes.

Immune Suppression:

Dogs were immune suppressed by daily administration of dexamethasone (0.4 mg/lb body weight) for 5 days beginning 13 weeks post-challenge.

Clinical Observations:

Dogs were observed daily for limb/joint disorders including stiffness (reluctant to put full weight on limbs), limping (favoring a limb while walking or running), or lameness (non-weight bearing). Scoring was made by the consensus of at least two observers, and dogs were examined by the Attending Veterinarian to rule out any other external injuries.

Necropsy:

Dogs that had limb/joint disorders for at least 3 consecutive observation periods were euthanized and necropsied. Tissue samples from the elbow, carpus, knee, tarsus, heart, spleen, bladder, and both kidneys were collected and processed for isolation of *B. burgdorferi* by culture. Joint tissues were cultured in individual tubes containing 9 mL BSK+G. Other tissues (heart, spleen, urinary bladder, and kidneys) were combined with 9 mL BSK+G, homogenized thoroughly with a stomacher, and a 1 mL amount was transferred to a separate tube containing 9 mL of fresh BSK+G. Cultures were incubated at 35±2° C.

The remaining dogs were euthanized and necropsied at the end of the study. Tissue samples from these dogs were collected from the joint capsule and tendon of the elbow, carpus, knee, and tarsus and stored in 10% buffered formalin for histopathology examination. In addition, samples from the joint capsules of the elbow, carpus, knee, and tarsus were placed into individual tubes containing 9 mL BSK+G or BSK+G with antibiotics and incubated at 35±2° C. for 3 weeks.

Western Blotting:

Western blotting was performed using standard techniques. *B. burgdorferi* ss 297 was boiled in sample buffer for 5 min and 150 μg of total protein was loaded onto a 0.1% SDS-12% polyacrylamide gel (4% polyacrylamide stacking gel without comb). Protein concentrations were determined with a protein determination kit, and two gels were run simultaneously in an electrophoresis unit. After electrophoresis, proteins were transferred to nitrocellulose, and the nitrocellulose was cut into strips and blocked with PBS-0.3% TWEEN 20 for 30 min at 22° C. Strips were incubated for 1 hour at 22° C. with dog serum diluted 1:100 and washed three times with PBS-0.05% TWEEN 20. Horseradish peroxidase-labeled anti-dog IgG (Kirkegaard & Perry Laboratories, Gaithersburg, Md.) was added, and the strips were incubated for 30 min at 22° C. before developing with the TMB Membrane Peroxidase Substrate System (Kirkegaard & Perry Laboratories, Gaithersburg, Md.).

B. Results

Safety of the Vaccine:

Dogs remained clinically normal following vaccination, including no increases in rectal temperature. Dogs vaccinated with the vaccine did however develop slight swelling at the injection site that resolved within 8 days. The largest reaction measured 1×1×0.5 cm (24 hour post-vaccination).

Post-Vaccination Serology:

Vaccination with placebo failed to induce antibodies specific for *B. burgdorferi* ss. In contrast, vaccination with the vaccine induced significant levels of borreliacidal antibodies detected by using *B. burgdorferi* ss isolates S-1-10 or 50772. The mean titer of borreliacidal antibodies detected by using S-1-10 peaked one week after the booster vaccination (study day 28) and remained detectable at study day 197 (Table 6 below). Similarly, high concentrations of borreliacidal antibodies specific for isolate 50772 were present by study day 28 and remained elevated at study day 43 and detectable at study day 197 (Table 7 below).

TABLE 6

Mean titers[a] (n = 15) of borreliacidal activity[b] after vaccination with the vaccine.

| Group | Day −3 | Day 21 | Day 28 | Day 35 | Day 43 | Day 78 | Day 106 | Day 134 | Day 162 | Day 197 |
|---|---|---|---|---|---|---|---|---|---|---|
| Vaccinates | ND[c] | >211 | >8128 | >6160 | >4889 | 1404 | 970 | 970 | 1016 | 220 |
| Controls | ND | ND | ND | ND | ND | ND | ND | ND | ND | ND |

[a]Reciprocal dilution.
[b]Detected by using borreliacidal antibody test with B. burgdorferi ss S-1-10.
[c]ND = None detected.

TABLE 7

Mean titers[a] (n = 15) of borreliacidal activity[b] after vaccination with the vaccine.

| Group | Day −3 | Day 21 | Day 28 | Day 35 | Day 43 | Day 78 | Day 106 | Day 134 | Day 162 | Day 197 |
|---|---|---|---|---|---|---|---|---|---|---|
| Vaccinates | ND[c] | ND | 1470 | 884 | 221 | 50 | 48 | 46 | 42 | 42 |
| Controls | ND | ND | ND | ND | ND | N/A[d] | N/A | N/A | N/A | N/A |

[a]Reciprocal dilution.
[b]Detected by using borreliacidal antibody test with B. burgdorferi ss 50772.
[c]ND = None detected.
[d]N/A = Not applicable.

Confirmation of OspA and OspC Borreliacidal Antibodies.

To confirm that the borreliacidal activity was due to OspA and OspC borreliacidal antibodies, immune sera from five dogs vaccinated with the vaccine were passed over separate columns containing rOspA or rOspC and the effects on the borreliacidal activities were examined. Removing OspA-specific or OspC-specific antibodies by adsorbing the sera with the recombinant proteins significantly ($\geq$4-fold reduction) decreased the borreliacidal activity detected by using the B. burgdorferi ss S-1-10 or 50772 isolates, respectively. The collective findings therefore confirmed the vaccine induced significant levels of OspA and OspC borreliacidal antibodies, and the borreliacidal activities detected by the B. burgdorferi ss S-1-10 or 50772 were almost entirely specific OspA or OspC borreliacidal antibodies, respectively. See Table 8 below.

TABLE 8

Effect of removing OspA or OspC antibodies on borreliacidal activity in sera from dogs (n = 5) vaccinated with the vaccine.

| | Borreliacidal Antibody Titer[a]: | | | |
|---|---|---|---|---|
| | OspA[b] | | OspC[c] | |
| Serum | before absorption | after absorption | before absorption | after absorption |
| 1 | 5120 | 160 | 5120 | 640 |
| 2 | 2560 | 160 | 5120 | 320 |
| 3 | 10240 | ND[d] | 5120 | 320 |
| 4 | 2560 | ND | 1280 | 160 |
| 5 | 1280 | 80 | 2560 | 320 |
| OspA control | 2560 | ND | — | — |
| OspC control | — | — | 2560 | ND |

[a]Reciprocal dilution.
[b]Sera collected on study day 43.
[c]Sera collected on study day 28.
[d]ND = None detected.

Confirmation of OspC7-specific borreliacidal antibodies

To confirm that the OspC borreliacidal antibodies contained a significant proportion of borreliacidal antibodies specific for OspC7, immune sera from five dogs vaccinated with the vaccine were passed over a column containing rOspC7, and the effects on the borreliacidal activity were examined. Removing the OspC7-specific antibodies by adsorbing the sera with the recombinant OspC7 protein significantly (2- to 4-fold reduction) decreased the borreliacidal activity detected by using the B. burgdorferi ss 50772 isolate. Therefore, the findings confirmed that the vaccine induced significant levels of OspC borreliacidal antibodies specific for the conserved OspC7 epitope. See Table 9 below.

TABLE 9

Effect of removing OspC7 antibodies on borreliacidal activity in sera from dogs (n = 5) vaccinated with the vaccine.

| | Borreliacidal Antibody Titer[a]: | |
|---|---|---|
| Serum | before absorption | after absorption |
| 1 | 20480 | 5120 |
| 2 | 10240 | 5120 |
| 3 | 10240 | 2560 |
| 4 | 5120 | 2560 |
| 5 | 10240 | 2560 |
| OspC control | 2560 | ND |

[a]Reciprocal dilution.
[b]Sera collected on study day 28.
[c]ND = None detected.

Ability of the OspA and OspC Borreliacidal Antibodies to Sterilize Infected Ticks:

Examining the midguts of the ticks that fed on the vaccinated or control dogs confirmed that the OspA and OspC borreliacidal antibodies induced by the vaccine had sterilized the ticks. B. burgdorferi ss were detected in the tick smears from 34 (32%) of 106 female ticks that had fed on 13 of 15 placebo-vaccinated dogs (Table 10 below). In contrast, no spirochetes (0 of 99) were detected in the midguts from the female ticks that fed on dogs vaccinated with the vaccine (p<0.0001).

TABLE 10

Detection of B. burgdorferi ss in female ticks removed from vaccinated or control dogs.

| Treatment Group | Female Ticks Processed (Engorged and Not engorged) | Smears Positive for B. burgdorferi | Total No. of Dogs Positive |
|---|---|---|---|
| Vaccinates | 99/151 (61%) | 0/99 (0%) | 0/15 |
| Controls | 106/148 (64%) | 34/106 (32%) | 13/15* |

*p < 0.0001

Ability of the Vaccine to Prevent Recovery of B. burgdorferi ss from the Skin:

The vaccine-induced borreliacidal antibodies also prevented the spirochetes from colonizing the skin. B. burgdorferi ss were recovered from 56 (79%) of 71 biopsies collected from the placebo-vaccinated dogs at monthly intervals following tick-challenge (Table 11 below) and spirochetes were recovered from at least one skin biopsy from 14 (93%) of the 15 dogs. In contrast, B. burgdorferi ss were not recovered from any skin biopsies collected from the dogs vaccinated with the vaccine (p<0.0001).

TABLE 11

Isolation of B. burgdorferi ss from the skin of vaccinated or non-vaccinated control dogs.

| Treatment Group | Day 78 | Day 106 | Day 134 | Day 162 | Day 197 | Total Biopsies Positive | Total No. of Dogs Positive |
|---|---|---|---|---|---|---|---|
| Vaccinated | 0/15 | 0/15 | 0/15 | 0/15 | 0/13 | 0/73 (0%) | 0/15 (0%) |
| Controls | 12/15 | 13/15 | 11/15 | 11/14 | 9/12 | 56/71 (79%) | 14/15* (93%) |

P < 0.0001

Figure 2A:
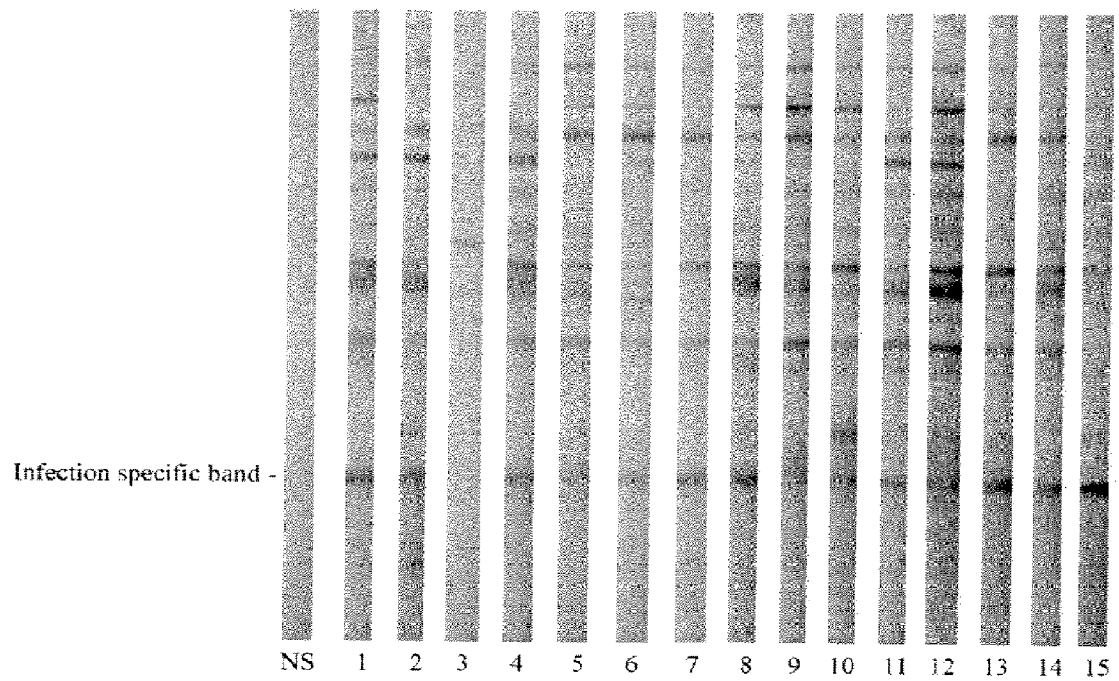
FIG. 2A is a Western blot of a normal dog serum control (NS) or sera from separate cohorts of individual dogs (numbered from 1-15) after vaccination with placebo and challenge with *B. burgdorferi* ss-infected ticks (study day 134).
Figure 2B:
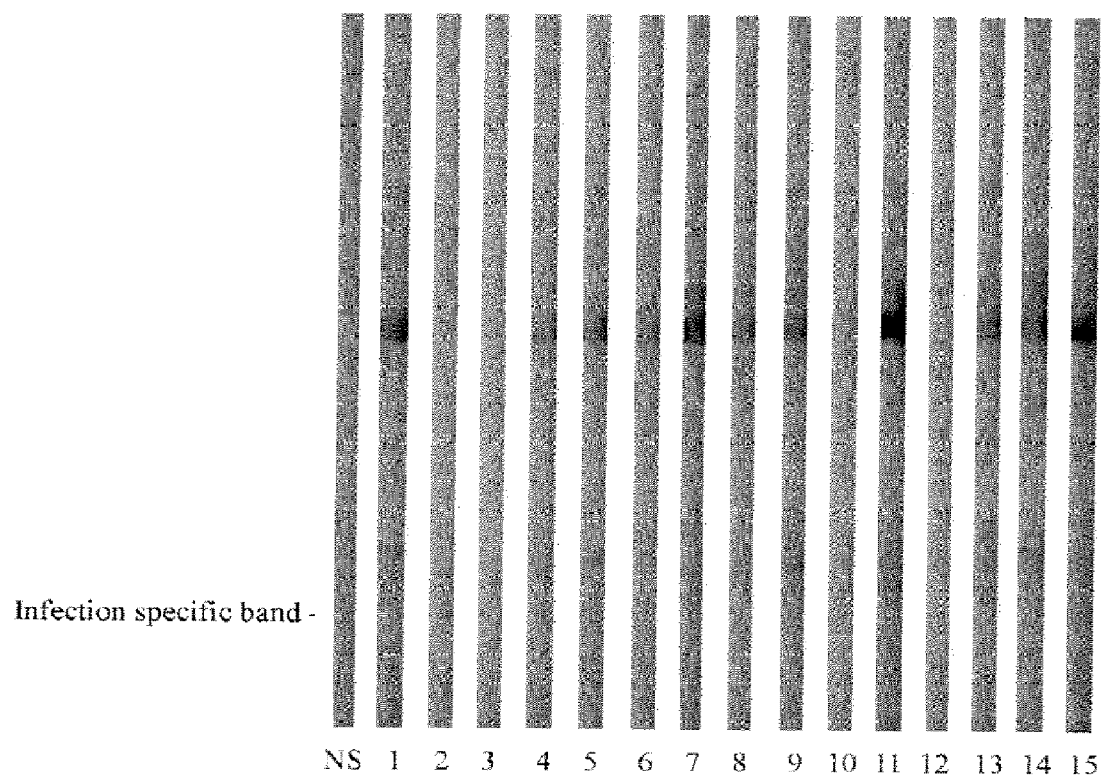
FIG. 2B is a Western blot of a normal dog serum control (NS) or sera from separate cohorts of individual dogs (numbered from 1-15) after vaccination with the test product. Note the presence of the infection-specific 20 kDa antibodies in 14 (93%) dogs vaccinated with placebo (FIG. 2A) and 0 (p<0.0001) dogs vaccinated with the test product (FIG. 2B).

Ability of the Vaccine to Prevent Serologic Evidence of Infection:

The vaccine also prevented the development of Lyme disease-specific antibodies. A previous investigation (SPAHC Report B01-184-01R) confirmed that infection with B. burgdorferi ss reliably induced dog antibodies that bound an approximately 20 kDa protein, and the response was not induced by the vaccine (FIG. 1). In the current study, antibodies that bound the infection-specific 20 kDa protein were detected readily in the immune sera from 14 (93%) of the 15 placebo-vaccinated control dogs (FIG. 2A). In addition, the serum that did not contain any 20 kDa protein antibodies was collected from the control dog that also failed to yield spirochetes from the skin. In contrast, 20 kDa protein antibodies were not produced (p<0.0001) by any of the dogs vaccinated with the vaccine (FIG. 2B).

In addition, dogs with Lyme disease produce non-OspC borreliacidal antibodies that are also detectable by using the B. burgdorferi ss 50772 isolate (Callister et al., J. Clin. Microbiol. 2000, 38:3670-3674). The specific target of the response is unknown, but the antibodies provide highly specific serodiagnostic confirmation of infection. Dogs vaccinated with the vaccine were already producing OspC borreliacidal antibodies, but no dogs developed a significant ($\geq$4-fold) increase in the level of B. burgdorferi ss 50772-specific borreliacidal antibodies after the tick challenge. It was therefore highly unlikely the vaccinated dogs were infected with spirochetes. In contrast, borreliacidal antibodies were not produced by the placebo-vaccinated dogs prior to challenge, but 10 (67%; p=0.0002) of the 15 dogs developed significant levels (titers $\geq$1:640) of borreliacidal antibodies detected by using B. burgdorferi ss 50772 after the ticks were allowed to feed (Table 12 below).

TABLE 12

Mean titers[a] of borreliacidal antibodies[b] after tick challenge.

| Treatment Group | Day 78 | Day 106 | Day 134 | Day 162 | Day 197 | Total No. of Dogs with Increase Titers |
|---|---|---|---|---|---|---|
| Vaccinates | 50 | 48 | 46 | 42 | 42 | 0/15 |
| Controls | >121 | >463 | >640 | >390 | >403 | 10/15* |

*p = 0.0002
[a]Reciprocal dilution.
[b]Detected by using B. burgdorferi ss 50772.

Ability of the Vaccine to Prevent Frank Limb/Joint Disorders:

Previous studies (Summers et al., J. Comp. Path. 2005, 133:1-13, Wikle et al., J. Appl. Res. Vet. Med. 2006, 4:23-28) demonstrated that infection with B. burgdorferi ss only rarely cause frank limb/joint disorders (e.g., swelling, lameness) and our findings confirmed this. Only one (8%) placebo-vaccinated control dog developed a joint abnormality. The left front leg was stiff 9 weeks after the tick-challenge, and B. burgdorferi ss spirochetes were recovered from the elbow. However, the findings were not significant because two dogs vaccinated with the vaccine also developed stiffness in one or more limbs, but, in contrast to the dog that received placebo, spirochetes were not recovered from any tissues.

To exacerbate the development of frank symptoms, the remaining dogs were immunosuppressed. Subsequently, three placebo-vaccinated control dogs became lame, and B. burgdorferi ss were recovered from two of these dogs. In contrast, no immunosuppressed dogs vaccinated with the vaccine developed lameness. Thus, the collective findings suggested the vaccine prevented the development of Lyme arthritis, although the results were not significant (p=0.0996). However, see the additional data presented and discussed below.

Figure 3A:
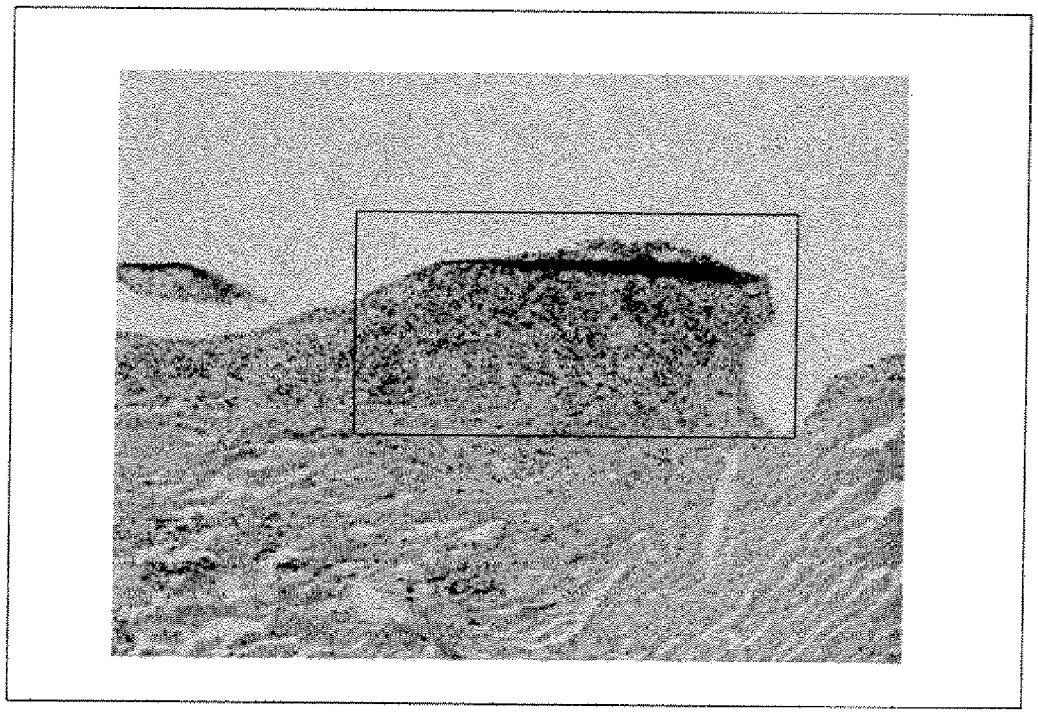
FIG. 3A is a representative example of the histopathological changes in the joints of placebo-vaccinated dogs that were infected with *B. burgdorferi* ss. The area within the rectangle represents a significant infiltration of neutrophils and mononuclear cells characteristic of canine Lyme arthritis
Figure 3B:
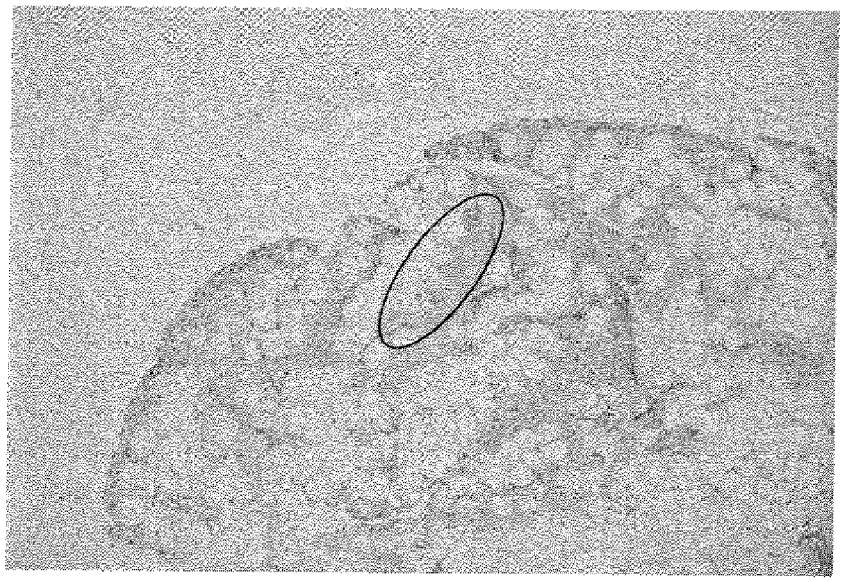
FIG. 3B is a representative example of the absence of histopathological changes in the joints of test product-vaccinated dogs that were infected with *B. burgdorferi* ss. The area within the oval is devoid of any infiltrating neutrophils and mononuclear cells.

Ability of the Vaccine to Prevent Erosive Changes Associated with B. burgdorferi ss Infection:

When the joints of the dogs discussed above were examined microscopically, however, the findings clearly demonstrated the effectiveness of the vaccine. The joint capsules from the remaining dogs (n=13) vaccinated with the vaccine were normal. In contrast, one or more joint tissues from 6 (p=0.0034) of the 11 remaining placebo-vaccinated control dogs (Table 7 above) had significant inflammation characterized by infiltration of neutrophils and mononuclear cells (FIG. 3). Moreover, B. burgdorferi ss were not recovered from any tissues from the dogs vaccinated with the vaccine, but spirochetes were recovered from joint tissues from 5 (83%) of the 6 placebo-vaccinated control dogs with erosive changes. The collective findings therefore, confirmed the vaccine prevented canine Lyme arthritis and also corroborated previous reports that the syndrome is characterized most often by subclinical synovitis (Summers et al., J. Comp. Path. 2005, 133:1-13; Wikle et al., J. Appl. Res. Vet. Med. 2006, 4:23-28).

Example 7

Specificity of Naturally-Occurring Borreliacidal Antibodies Directed to the OSPC7 Epitope Data confirming that borreliacidal antibodies elicited in a mammal against OspC7 are specific have been obtained by analyzing sera from individuals (human) with and without a history of Lyme disease or Lyme-related symptoms, as follows.

A. Materials and Methods

1. Sera:

Normal sera from individuals with no previous history (chart-review) of Lyme disease or Lyme-related symptoms (n=36), uncharacterized sera from blood donors (n=100) or individuals undergoing cholesterol screenings (n=100), or sera from volunteers with blood factors or illnesses that commonly cross-react with *B. burgdorferi* ss antigens, including antinuclear antibodies (n=20), rheumatoid factor (n=20), mononucleosis (n=10), cytomegalovirus (n=10), syphilis (n=13) or Rocky Mountain spotted fever (n=4), were from archived samples stored at −20° C. Lyme disease sera were collected from patients evaluated at Gundersen Lutheran Medical Center during 2003 or 2004. Sera (n=86) from patients with erythema migrans (EM) that fulfilled the CDC surveillance criterion (Centers for Disease Control and Prevention. Morb. Mort. Wkly. Rep. 1990, 39:19-21.) were classified as likely Lyme, sera (n=22) from patients with tick exposures and atypical skin lesions were classified as probable Lyme (n=49), and sera from patients with tick exposure and constitutional symptoms that included primarily headache, fever, myalgia, and arthralgia were classified as possible Lyme. The sera were collected during the initial visit, stored at −20° C., and blinded prior to testing.

OspC7 peptide. The 7-aa OspC7 peptide (AESPKKP; SEQ ID NO: 1) was synthesized at the University of Wisconsin Biotechnology Center (Madison, Wis.) by using an automated synthesizer (Protein Technologies) and the Fmoc method (Fields, et al., Peptide Res. 1991, 4:95-101). Following synthesis, the amino-terminal end of the peptide was biotinylated manually by HBTU activation and purified by high-pressure liquid chromatography. Composition was confirmed using matrix-assisted laser desorption ionization-time of flight (MALDI-TOF) mass spectrometry (predicted mass 1095.4; observed mass 1095.8).

OspC7 ELISA. Individual wells of microtiter plates (Immunolon 2 HB, Thermo Labsystems, Franklin, Mass.) were coated with 100 µL of a 4 µg/ml suspension of streptavidin (Pierce, Rockland, Ill.) contained in carbonate buffer (90 mM $NaHCO_3$, 60 mM $Na_2CO_3$; pH 9.6) and incubated overnight at 4° C. Following incubation, plates were washed five times with Tris-buffered saline (TBS-T; 13 mM Tris HCl, 3 mM Tris base, 140 mM NaCl, 2.7 mM KCl; pH 7.4) containing 0.05% Tween 20. After washing, 2004 of blocking buffer (15 mM NaCl, 10 mM Tris HCl, 3% fetal bovine serum, 0.05% Tween 20) containing 1 µg/mL of biotinylated OspC7 peptide was added to each well and incubated with rotation (150 rpm) for 1 hour at room temperature. Plates were washed three times with TBS-T and reacted with 1004 amounts of sera diluted 1:200 in blocking buffer for 1 hour at room temperature. The secondary antibody was peroxidase-conjugated goat anti-human IgM and IgG (Kirkegaard Perry Laboratories, Gaithersburg, Md.) diluted 1/15,000 in blocking buffer. After incubation for one hour, the bound secondary antibody was quantified by the addition of o-phenylenediamine and hydrogen peroxide in citrate buffer (Sigma, St. Louis, Mo.) and determination of the OD at 490 nm (SpectraMax 250; Molecular Devices, Sunnyvale, Calif.).

B. Results

Figure 4:
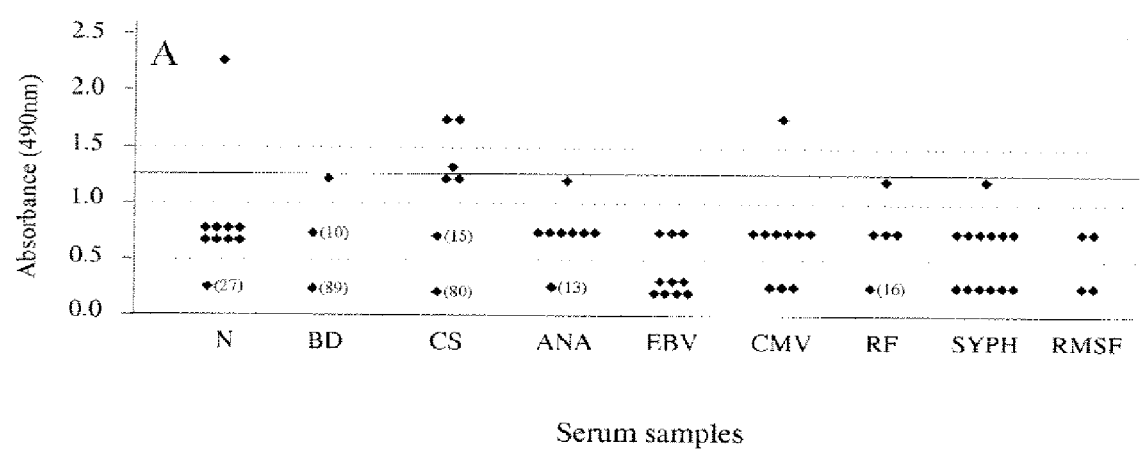
FIG. 4 illustrates determination of OspC7 ELISA reactivity using normal sera (N) from individuals with no previous history (chart-review) of Lyme or Lyme-related symptoms (n=36), uncharacterized sera from blood donors (BD, n=100) or individuals undergoing cholesterol screenings (CS, n=100), or sera from volunteers with blood factors or illnesses that commonly cross-react with *B. burgdorferi* ss antigens, including antinuclear antibodies (ANA, n=20), rheumatoid factor (RF, n=20), mononucleosis (EBV, n=10), cytomegalovirus (CMV, n=10), syphilis (SYPH, n=13) or Rocky Mountain spotted fever (RMSF n=4). The solid line denotes three standard deviations above the mean absorbance value of the normal and potential cross-reactive sera. Values above the line correspond to positive results to a 99% probability (1% background value).
Figure 5:
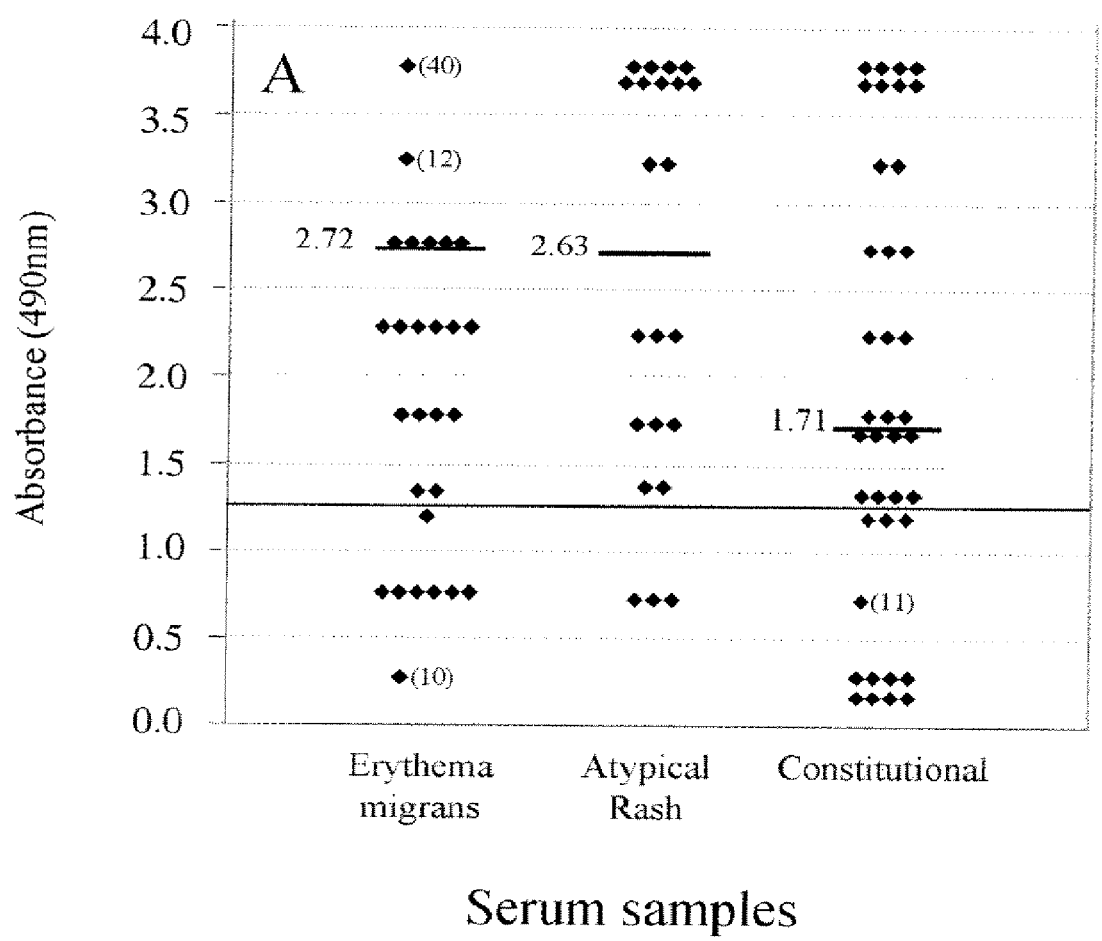
FIG. 5 illustrates OspC7 ELISA reactivity using sera from probable Lyme disease patients with erythema migrans (n=86) representing patients with typical Lyme lesions, likely Lyme patients with "atypical lesions" (n=22), and possible Lyme patients with constitutional symptoms (n=49) [earliest clinical signs]. The solid line denotes three standard deviations above the mean absorbance value of the normal and potential cross-reactive sera.

In previous studies (Jobe et al., *Clin. Diagn. Lab. Immuno.* 2003, 10:573-578, Lovrich et al., *Clin. Diagn. Lab. Immunol.* 2005, 12:746-751), a highly conserved immunodominant OspC borreliacidal antibody epitope was localized to the region within the 7 amino acids nearest the C-terminus (OspC7). To confirm the epitope induced antibodies specific to infection with *Borrelia* spp., the reactivities of an ELISA that used OspC7 using sera from patients with Lyme disease (FIG. 5) and sera from normal subjects or patients with other illnesses likely to produce antibodies that could also bind *Borrelia* spp. proteins (FIG. 4) were compared. In FIGS. 4 and 5, the line at Absorbance 1.25 defines three standard deviations above the mean absorbance of the normal and potentially cross-reactive sera. Any results that fall above the line therefore have a 99% probability that the reactivity is significant (true positive). Significant reactivity was detected only rarely in the normal or potentially cross-reactive sera (FIG. 4). It should also be noted that the majority of the positive results were obtained using sera that could have come from Lyme disease patients, because the sera (CS) were obtained from a group of 100 patients being seen at Gundersen Lutheran Medical Center for a variety of ailments. The region is a highly endemic focus of Lyme disease, and the identities and clinical histories of the patients were unknown. In contrast, positive sera were not detected in serum samples (n=100) collected randomly from blood donors (BD) in Milwaukee, a non-endemic region of Wisconsin.

In addition, positive results (greater than 3 standard deviations above the mean of the sera that should be non-reactive—FIG. 4) were detected commonly in the sera from the Lyme disease patients and the absorbance values were high (FIG. 5). The collective findings therefore confirmed the high specificity of the antibodies directed against the OspC7 epitope and the immunodominance of the response during human Lyme disease.

Summarizing the above-exemplified data, groups (15 dogs) of 8 week-old puppies were vaccinated and boosted with a vaccine that contained $5.0\times10^8$ *B. burgdorferi* ss 50772, $2.5\times10^7$ *B. burgdorferi* S-1-10 ss and 5% Emulsigen® or a placebo that contained only 5% Emulsigen®. The vaccine caused slight swelling at the site of the injection that resolved quickly. More significantly, the vaccine induced high concentrations of borreliacidal OspA and OspC antibodies that peaked a week after the booster vaccination and remained detectable for the duration of the study. In addition, a significant proportion of the OspC borreliacidal antibodies were specific for the highly conserved epitope within OspC7.

*B. burgdorferi* ss-infected female *I. scapularis* ticks were then allowed to feed on the vaccinated dogs, and an examination of the midguts from the ticks confirmed that the OspA and OspC borreliacidal antibodies in the bloodmeal completely eliminated *B. burgdorferi* ss. Specifically, *B. burgdorferi* ss were detected in 34 (32%) ticks collected from the control dogs vaccinated with placebo and not detected in ticks (n=99) that fed on the dogs vaccinated with the vaccine (p<0.0001). In addition, the vaccine recipients remained negative for Lyme disease by several indirect and direct methods used commonly to confirm infection. In contrast, 10 (67%) control dogs produced antibodies against an "infection-specific" 20 kDa *B. burgdorferi* ss protein and 8 (53%) produced "infection-specific" borreliacidal antibodies. Moreover, four (27%) dogs developed persistent lameness, and *B. burgdorferi* ss were recovered from the joints of 3 (75%) of the 4 lame animals. In addition, inflammatory infiltrates developed in the joint capsules of 6 (55%) of the 11 placebo-vaccinated dogs examined. More compelling, *B. burgdorferi* ss were recovered from the skin and joints of 14

(93%) and 8 (53%) control dogs, respectively, while spirochetes were not recovered from dogs vaccinated with the test product. Thus, the inventive Lyme disease vaccine caused minimal side effects and provided complete protection against infection with B. burgdorferi ss.

Example 8

Duration of Immunity of the Vaccine Comprising B. burgdorferi ss Isolates S-1-10 and 50772

A. Materials and Methods
Animals:
Materials and methods are described in Example 6 above.
Vaccination and Collection of Sera:
Dogs were vaccinated subcutaneously in the neck with a 1 mL dose of the vaccine and boosted with an additional 1 mL dose after 21 days. Whole blood was collected prior to the initial (study day −4) and booster vaccination (study day 21) and also on study days 28, 35, 49, 79, 114, 142, 175, 210, 238, 266, 302, 322, 357, and 394 by venipuncture of the jugular vein. The serum was separated by centrifugation and stored at −20° C. until tested.
Post-vaccination Observations:
Dogs were observed daily.
Tick Challenge:
One year after the second vaccination, dogs were shaved on the right side of the thoracic cavity, and 10 female and 10 male B. burgdorferi-infected I. scapularis ticks were placed in a rubber cup that was secured to the shaved area with tape and bandage wrap. The ticks were allowed to feed for 7 days.
Detection of B. burgdorferi ss in Ticks:
Detection was performed in the manner described in Example 6 above.
Blood Samples:
Whole blood was collected in serum separation transport (SST) tubes on study days 43 post-challenge (PC), 77 PC, 112 PC, 147 PC, 174 PC, and 241 PC, and the serum separated and stored at −20° C. until tested.
Detection of Borreliacidal Antibodies:
OspA and OspC borreliacidal antibodies were detected by flow cytometry as described in Examples 1 and 2 above.
Skin Biopsies:
Skin biopsies were taken from sites adjacent to tick attachment on study days 43 post-challenge (PC), 77 PC, 112 PC, 147 PC, 174 PC, and 241 PC with a disposable 4 mm puncture device. The biopsies were processed as described in Example 6 above.
Immune Suppression:
Dogs were immune suppressed by daily administration of dexamethasone (0.4 mg/lb body weight) for 5 days beginning at approximately 20 weeks post-challenge.
Clinical Observations:
Clinical observations were performed as in Example 6 above.
Necropsy:
Necropsy was performed as in Example 6 above.
B. Results
Post-Vaccination Serology:
Vaccination with a placebo failed to induce antibodies specific for B. burgdorferi ss. In contrast, vaccination with the vaccine induced significant levels of borreliacidal antibodies detected by using B. burgdorferi ss isolates S-1-10 and 50772. The mean borreliacidal antibody titer against S-1-10 peaked one week (study day 28) after the booster vaccination, and the response remained detectable until study day 394 (Table 13). Similarly, high concentrations of borreliacidal antibodies specific for isolate 50772 were detected on study day 28, titers remained elevated on study day 49, and low levels remained detectable after 79 days (Table 14).

TABLE 13

Mean titers[a] (n = 15) of borreliacidal activity[b] after vaccination with the vaccine.

| Group | Day −4 | Day 21 | Day 28 | Day 35 | Day 49 | Day 79 | Day 114 | Day 142 |
|---|---|---|---|---|---|---|---|---|
| Vaccinates | ND[c] | 192 | >7075 | >5120 | >4457 | 735 | 926 | 532 |
| Controls | ND | ND | ND | ND | ND | ND | ND | ND |

| Group | Day 175 | Day 210 | Day 238 | Day 266 | Day 302 | Day 322 | Day 357 | Day 394 |
|---|---|---|---|---|---|---|---|---|
| Vaccinates | 702 | 611 | 926 | 557 | 508 | 351 | 211 | 175 |
| Controls | ND | ND | ND | ND | ND | ND | ND | ND |

[a]Reciprocal dilution.
[b]Detected by using borreliacidal antibody test with B. burgdorferi ss S-1-10.
[c]ND = None detected.z

TABLE 14

Mean titers[a] (n = 15) of borreliacidal activity[b] after vaccination with the vaccine.

| Group | Day −4 | Day 21 | Day 28 | Day 35 | Day 49 | Day 79 | Day 114 | Day 142 |
|---|---|---|---|---|---|---|---|---|
| Vaccinates | ND[c] | 40 | 1689 | 532 | 69 | 41 | ND | ND |
| Controls | ND | ND | ND | ND | ND | ND | ND | ND |

| Group | Day 175 | Day 210 | Day 238 | Day 266 | Day 302 | Day 322 | Day 357 | Day 394 |
|---|---|---|---|---|---|---|---|---|
| Vaccinates | ND | ND | ND | ND | ND | ND | ND | ND |
| Controls | ND | ND | ND | ND | ND | ND | ND | ND |

[a]Reciprocal dilution.
[b]Detected by using borreliacidal antibody test with B. burgdorferi ss 50772.
[c]ND = None detected.

Ability of the OspA and OspC Borreliacidal Antibodies to Sterilize Infected Ticks:

Examining the midguts of the ticks that fed on the vaccinated or control dogs confirmed that the OspA and OspC borreliacidal antibodies induced by the vaccine had sterilized the ticks. B. burgdorferi ss were detected in the tick smears from 15 (16%) of 95 female ticks that had fed on 12 of 15 placebo-vaccinated dogs (Table 15). In contrast, B. burgdorferi ss were detected in the tick smears from only 2 (3%) of 75 female ticks that had fed on 2 of 15 vaccinated dogs (p=0.0003).

TABLE 15

Detection of B. burgdorferi ss in female ticks removed from vaccinated or control dogs.

| Treatment Group | [a]Female Ticks Processed | Smears Positive for B. burgdorferi | Total No. of Dogs Positive |
|---|---|---|---|
| Vaccinates | 75/148 (51%) | 2/75 (3%) | 2/15 |
| Controls | 95/146 (65%) | 15/95 (16%) | 12/15* |

*p = 0.0003
[a]Engorged and not engorged

Ability of the Vaccine to Prevent Recovery of B. burgdorferi ss from the Skin:

The vaccine-induced borreliacidal antibodies also prevented a sustained infection of B. burgdorferi organisms in the skin. B. burgdorferi ss were recovered from 33 (44%) of 75 biopsies collected from the placebo-vaccinated dogs at monthly intervals following tick-challenge (Table 16). In contrast, B. burgdorferi ss were recovered from only 6 (8%) of 75 biopsies collected from the dogs vaccinated with the vaccine (p<0.0001). Spirochetes were recovered from at least one skin biopsy from 10 (67%) of the 15 control dogs, compared to 6 (40%) of the 15 vaccinated dogs. However, isolations from the vaccinated dogs were limited to only the first month post-challenge, whereas, 8 (80%) of the 10 culture positive control dogs had B. burgdorferi-positive skin biopsy cultures throughout the following months of the study.

TABLE 16

Isolation of B. burgdorferi ss from the skin of vaccinated or non vaccinated control dogs.

| Treatment Group | Day 43 PC | Day 77 PC | Day 112 PC | Day 147 PC | Day 174 PC | Biopsies Positive (Total)[b] | Dogs Positive (Total)[c] | Dogs Positive (Total)[d] |
|---|---|---|---|---|---|---|---|---|
| Vaccinates (A) | 6/15 | 0/15 | 0/15 | 0/15 | 0/15 | 6/75 (8%) | 6/15 (40%) | 0/6 (0%) |
| Controls (B) | 9/15 | 8/15* | 7/15[a]* | 6/15* | 3/15 | 33/75** (44%) | 10/15 (67%) | 8/10 (80%) |

[a]One new dog.
[b]Total Biopsies that were positive.
[c]Total number of Dogs that were positive.
[b]Total number of dogs that were positive after the first month.
*p < 0.05
**p < 0.0001

Ability of the Vaccine to Prevent Serologic Evidence of Infection:

The vaccine also prevented the development of Lyme disease-specific antibodies. Dogs with Lyme disease produce non-OspC borreliacidal antibodies that are also detectable by using the B. burgdorferi ss 50772 isolate (as described in Example 6). Significant, increased levels 4-fold increase) of borreliacidal antibodies against strain 50772 were observed post-challenge in 5 (33%) of the 15 placebo-vaccinated control dogs compared to none of the dogs vaccinated with the test vaccine.

TABLE 17

Mean titers[a] of borreliacidal antibodies[b] after tick challenge.

| Treatment Group | Day 43 PC | Day 77 PC | Day 112 PC | Day 147 PC | Day 174 PC | Total No. of Dogs with Increased Titers |
|---|---|---|---|---|---|---|
| Vaccinates | 40 | 40 | 40 | 40 | 40 | 0/15 |
| Controls | 48 | 66 | 88 | 88 | 106 | 5/15[c] |

[a]Reciprocal dilution.
[b]Detected by using B. burgdorferi ss 50772.
[c]≧4-fold increase titer Ability of the Vaccine to Prevent Frank Limb/Joint Disorders and Erosive Changes Associated with B. burgdorferi ss Infection:

Previous studies demonstrated that infection with B. burgdorferi ss only rarely causes frank limb/joint disorders (Example 6), and the tick challenge model has been shown to be less effective in older dogs. To exacerbate the development of frank symptoms, the dogs were immunosuppressed with dexamethasone approximately 3 months post-challenge. Four placebo-vaccinated control dogs either became lame or developed erosive lesions in the joint tissue. In contrast, none of the dogs vaccinated with a vaccine of the present invention developed any clinical signs of limb/joint disorders or the erosive lesions often seen in the joint tissue.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are hereby incorporated by reference in their entireties.

We claim:

1. A vaccine composition comprising an immunologically effective amount of organisms from a first strain of *B. burgdorferi*, wherein first stain is *B. burgdorferi* ss 50772 (ATCC No. PTA-439) and an immunologically effective amount of organisms of a second strain of *B. burgdorferi;* wherein said first strain exhibits an OspC antigen on its cell surface; and wherein said second strain exhibits an OspA antigen on its cell surface.

2. The vaccine of claim 1, wherein the immunologically effective amount of organisms from said first strain and said second strain of *Borrelia* have been inactivated.

3. The vaccine of claim 1, wherein OspC-borreliacidal antibodies are induced in a canine when said canine is immunized with said vaccine composition.

4. The vaccine composition of claim 3, wherein a significant proportion of the OspC-specific borreliocidal antibodies are specific for OspC7.

5. The vaccine composition of claim 1, wherein OspC-borreliacidal antibodies and OspA-borreliacidal antibodies are induced in a canine when said canine is immunized with said vaccine composition.

6. The vaccine composition of claim 2, wherein OspC-borreliacidal antibodies and OspA-borreliacidal antibodies are induced in a canine when said canine is immunized with said vaccine composition.

7. The vaccine composition of claim 1 comprising from about $1\times10^4$ to about $1\times10^{10}$ organisms per milliliter of the first strain and from about $1\times10^4$ to about $1\times10^{10}$ organisms per milliliter of the second strain.

8. The vaccine composition of claim 7 comprising from about $5.0\times10^8$ to about $5\times10^9$ organisms per milliliter of the first strain and from about $1.0\times10^8$ to about $5\times10^8$ organisms per milliliter of the second strain.

9. The vaccine composition of claim 2 further comprising a pharmaceutically acceptable adjuvant.

10. The vaccine composition of claim 1 further comprising a pharmaceutically acceptable immune stimulant.

11. The vaccine composition of claim 1 further comprising at least one non-*Borrelia* immunogen for eliciting protective immunity to a non-*Borrelia* pathogen.

12. The vaccine composition of claim 11, wherein the non-*Borrelia* immunogen is selected from the group consisting of canine distemper virus, canine adenovirus, canine parvovirus, canine parainfluenza virus, canine coronavirus, canine influenza virus, *Leptospira serovars, Leishmania* organisms, *Bordetella bronchiseptica, Mycoplasma* species, rabies virus, *Ehrlichia canis*, an *anaplasma* organisim, and combinations thereof.

13. The vaccine composition of claim 12, wherein the *Leptospira* serovars are selected from the group consisting of *Leptospira kirschneri* serovar grippotyphosa, *Leptospira interrogans* serovar canicola, *Leptospira interrogans* serovar icterohaemorrhagiae, *Leptospira interrogans* serovar pomona, and combinations thereof.

14. The vaccine composition of claim 12, wherein the *Mycoplasma* species comprises *Mycoplasma cynos.*

15. The vaccine composition of claim 2 comprising from about $1\times10^4$ to about $1\times10^{10}$ organisms per milliliter of the first strain and from about $1\times10^4$ to about $1\times10^{10}$ organisms per milliliter of the second strain.

16. The vaccine composition of claim 15 comprising from about $5.0\times10^8$ to about $5\times10^9$ organisms per milliliter of the first strain and from about $1.0\times10^8$ to about $5\times10^8$ organisms per milliliter of the second strain.

17. A method of immunizing a canine against a pathogenic *Borrelia* genospecies comprising injecting the canine with an immunologically effective amount of the vaccine of claim 2.

18. A method of immunizing a canine against a pathogenic *Borrelia* genospecies comprising injecting the canine with an immunologically effective amount of the vaccine of claim 1.

19. The method of claim 18 wherein the second strain is *B. burgdorferi* sensu stricto.

20. The method of claim 18 wherein the second strain is selected from the group consisting of *B. burgdorferi* ss S-1-10 (ATCC No. PTA-1680), *B. burgdorferi* ss B-31 (ATCC No. 35210), *B. afzelii* (ATCC No. 51567), *B. garinii* (ATCC Nos. 51383 or 51991), *B. burgdorferi* ss DK7, *B. burgdorferi* ss 61 BV3, *B. burgdorferi* ss ZS7, *B. burgdorferi* ss Pka, *B. burgdorferi* ss IP1, IP2, IP3, *B. burgdorferi* ss HII, *B. burgdorferi* ss P1F, *B. burgdorferi* ss Mil, *B. burgdorferi* ss 20006, *B. burgdorferi* ss 212, *B. burgdorferi* ss ESP1, *B. burgdorferi* ss Ne-56, *B. burgdorferi* ss Z136, *B. burgdorferi* ss ia, and combinations thereof.

21. The method of claim 18 wherein the immunized canine produces borreliacidal antibodies.

22. The method of claim 18 wherein the canine is injected with from about $5\times10^7$ to about $5\times10^9$ of each respective strain of *Borrelia* species.

23. The method of claim 17 wherein the immunized canine produces borreliacidal antibodies.

* * * * *

SEQUENCE LISTING

<160> NUMBER OF SEQ ID NOS: 1

<210> SEQ ID NO 1
<211> LENGTH: 7
<212> TYPE: PRT
<213> ORGANISM: Borrelia burgdorferi

<400> SEQUENCE: 1

Ala Glu Ser Pro Lys Lys Pro
1               5